United States Patent
Navkar et al.

(10) Patent No.: US 12,090,002 B2
(45) Date of Patent: Sep. 17, 2024

(54) SYSTEM AND METHODS FOR TELE-COLLABORATION IN MINIMALLY INVASIVE SURGERIES

(71) Applicants: Hamad Medical Corporation, Doha (QA); Qatar Foundation for Education, Science and Community Development, Doha (QA)

(72) Inventors: Nikhil Vishwas Navkar, Doha (QA); Abdulla Al-Ansari, Doha (QA); Julien Abi Nahed, Doha (QA)

(73) Assignees: QATAR FOUNDATION FOR EDUCATION, SCIENCE AND COMMUNITY DEVELOPMENT, Doha (QA); HAMAD MEDICAL CORPORATION, Doha (QA)

( * ) Notice: Subject to any disclaimer, the term of this patent is extended or adjusted under 35 U.S.C. 154(b) by 490 days.

(21) Appl. No.: 17/481,513

(22) Filed: Sep. 22, 2021

(65) Prior Publication Data

US 2022/0079705 A1   Mar. 17, 2022

Related U.S. Application Data

(63) Continuation-in-part of application No. PCT/QA2020/050005, filed on Mar. 22, 2020.

(Continued)

(51) Int. Cl.
*A61B 90/00* (2016.01)
*A61B 17/34* (2006.01)
(Continued)

(52) U.S. Cl.
CPC .......... *A61B 90/361* (2016.02); *A61B 17/34* (2013.01); *A61B 34/20* (2016.02); *G06F 3/014* (2013.01);
(Continued)

(58) Field of Classification Search
CPC ....... A61B 90/361; A61B 34/20; A61B 17/34; A61B 2034/2055; A61B 2034/2065;
(Continued)

(56) References Cited

U.S. PATENT DOCUMENTS 11,607,277 B2 * 3/2023 Calloway ................ G06T 11/00
2007/0248261 A1 * 10/2007 Zhou ...................... G06T 19/006
382/154

(Continued)

FOREIGN PATENT DOCUMENTS

WO   2018013773 A1   1/2018

OTHER PUBLICATIONS

Preliminary Report on Patentability for related International Application No. PCT/QA2020/050005; report dated Oct. 7, 2021; (9 pages).

(Continued)

*Primary Examiner* — Tom V Sheng
(74) *Attorney, Agent, or Firm* — K&L Gates LLP

(57) ABSTRACT

Disclosed is an immersive, augmented reality-based, enabling technology for tele-collaboration between a local surgeon and a remote surgeon during an MIS. The technology would provide realistic visual-cues to the local surgeon for the required movement of an actuated, high degree-of-freedom surgical tool during an MIS.

27 Claims, 37 Drawing Sheets
(26 of 37 Drawing Sheet(s) Filed in Color)

Related U.S. Application Data

(60) Provisional application No. 62/822,482, filed on Mar. 22, 2019.

(51) Int. Cl.

| | | |
|---|---|---|
| *A61B 34/20* | (2016.01) | |
| *G06F 3/01* | (2006.01) | |
| *G06F 3/03* | (2006.01) | |
| *G16H 20/40* | (2018.01) | |
| *G16H 30/40* | (2018.01) | |
| *G16H 40/20* | (2018.01) | |
| *G16H 40/67* | (2018.01) | |
| *G16H 80/00* | (2018.01) | |
| *A61B 17/00* | (2006.01) | |

(52) U.S. Cl.
CPC ............ *G06F 3/017* (2013.01); *G06F 3/0304* (2013.01); *G16H 20/40* (2018.01); *G16H 30/40* (2018.01); *G16H 40/20* (2018.01); *G16H 40/67* (2018.01); *G16H 80/00* (2018.01); *A61B 2017/00207* (2013.01); *A61B 2034/2055* (2016.02); *A61B 2034/2065* (2016.02); *A61B 2090/365* (2016.02); *A61B 2090/3945* (2016.02)

(58) Field of Classification Search
CPC ...... A61B 2090/365; A61B 2090/3945; A61B 2017/00207; G16H 20/40; G16H 40/67; G16H 40/20; G16H 30/40; G16H 80/00; G06F 3/014; G06F 3/017; G06F 3/0304
USPC .......................................................... 345/156
See application file for complete search history.

(56) References Cited

U.S. PATENT DOCUMENTS

| | | | |
|---|---|---|---|
| 2010/0167249 A1* | 7/2010 | Ryan | G09B 23/285 |
| | | | 434/267 |
| 2011/0238079 A1* | 9/2011 | Hannaford | A61B 34/76 |
| | | | 606/130 |
| 2014/0176661 A1 | 6/2014 | Smurro et al. | |
| 2016/0028994 A1 | 1/2016 | Reina et al. | |
| 2018/0185110 A1 | 7/2018 | Kumar et al. | |
| 2018/0325604 A1* | 11/2018 | Atarot | A61B 5/7475 |
| 2019/0007232 A1* | 1/2019 | Kim | H04L 12/283 |
| 2020/0000528 A1* | 1/2020 | Deodhar | A61B 1/015 |
| 2020/0054412 A1* | 2/2020 | Fuerst | A61B 17/00 |
| 2020/0388075 A1* | 12/2020 | Kazanzides | A61B 90/37 |
| 2021/0169605 A1* | 6/2021 | Calloway | A61B 90/36 |
| 2021/0378768 A1* | 12/2021 | Olson | A61B 34/20 |
| 2023/0083605 A1* | 3/2023 | Robinson | G06T 19/00 |
| | | | 606/1 |
| 2023/0139425 A1* | 5/2023 | Shademan | A61B 90/37 |
| | | | 700/245 |

OTHER PUBLICATIONS

International Search Report for related International Application No. PCT/QA2020/050005; report dated Oct. 9, 2020; (2 pages).
Written Opinion for related International Application No. PCT/QA2020/050005; report dated Oct. 9, 2020; (7 pages).
Davis, et al; "Virtual Interactive Presence in Global Surgical Education: International Collaboration through Augmented Reality"; Jun. 20, 2017; HHS Public Access; (16 pages).
Fuchs, et al.; "Augmented Reality Visualization for Laparoscopic Surgery"; University of North Carolina at Chapel Hill; (10 pages).
Chebbi, et al.; "A Collaborative virtual haptic environment for surgical training and tele-mentoring"; International Journal of Robotics and Automation; vol. 22, No. 1; 2007; (10 pages).

* cited by examiner

Operating Room 800

Remote Location 900

Registration Window 1100

Augmentation Window 1200

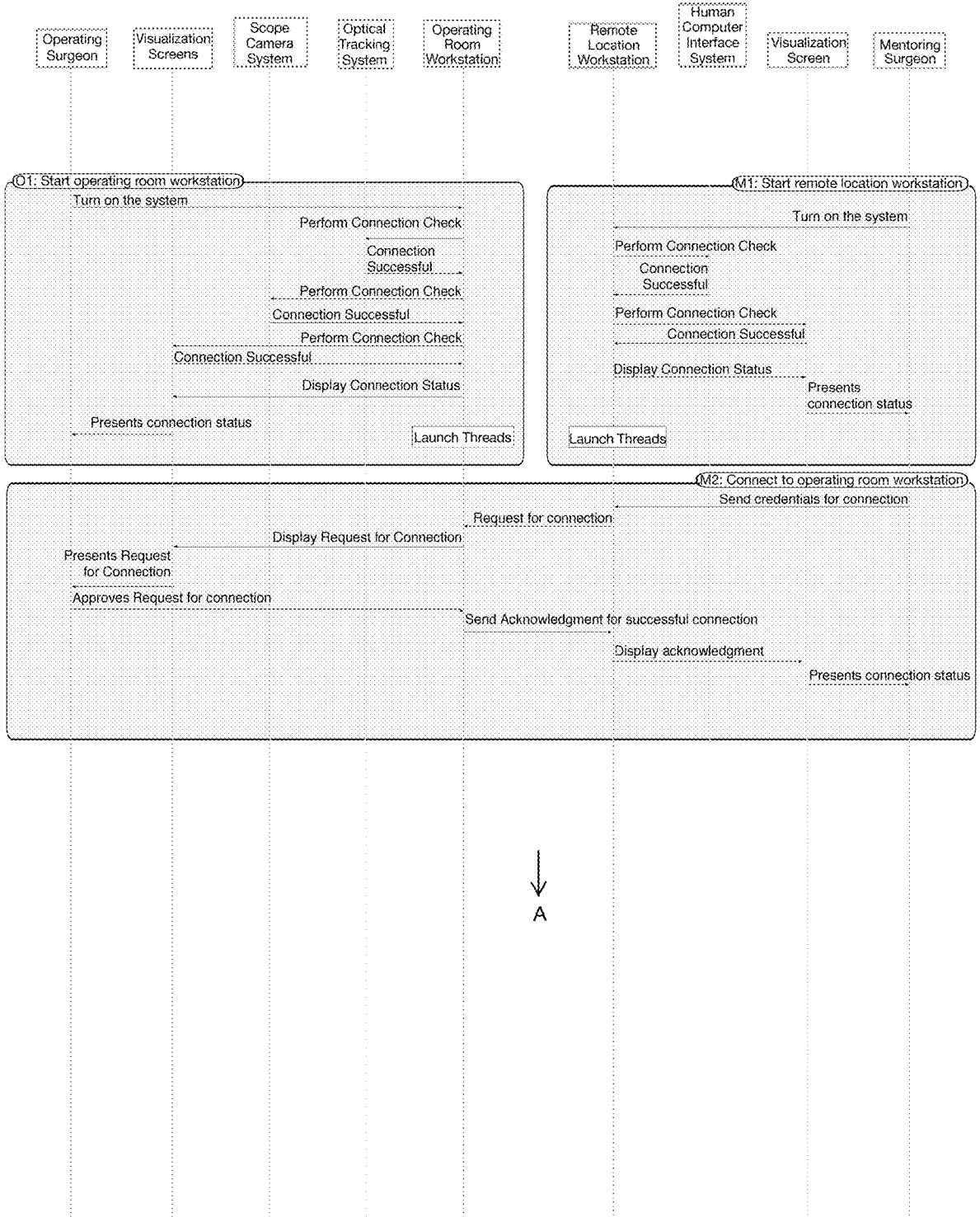

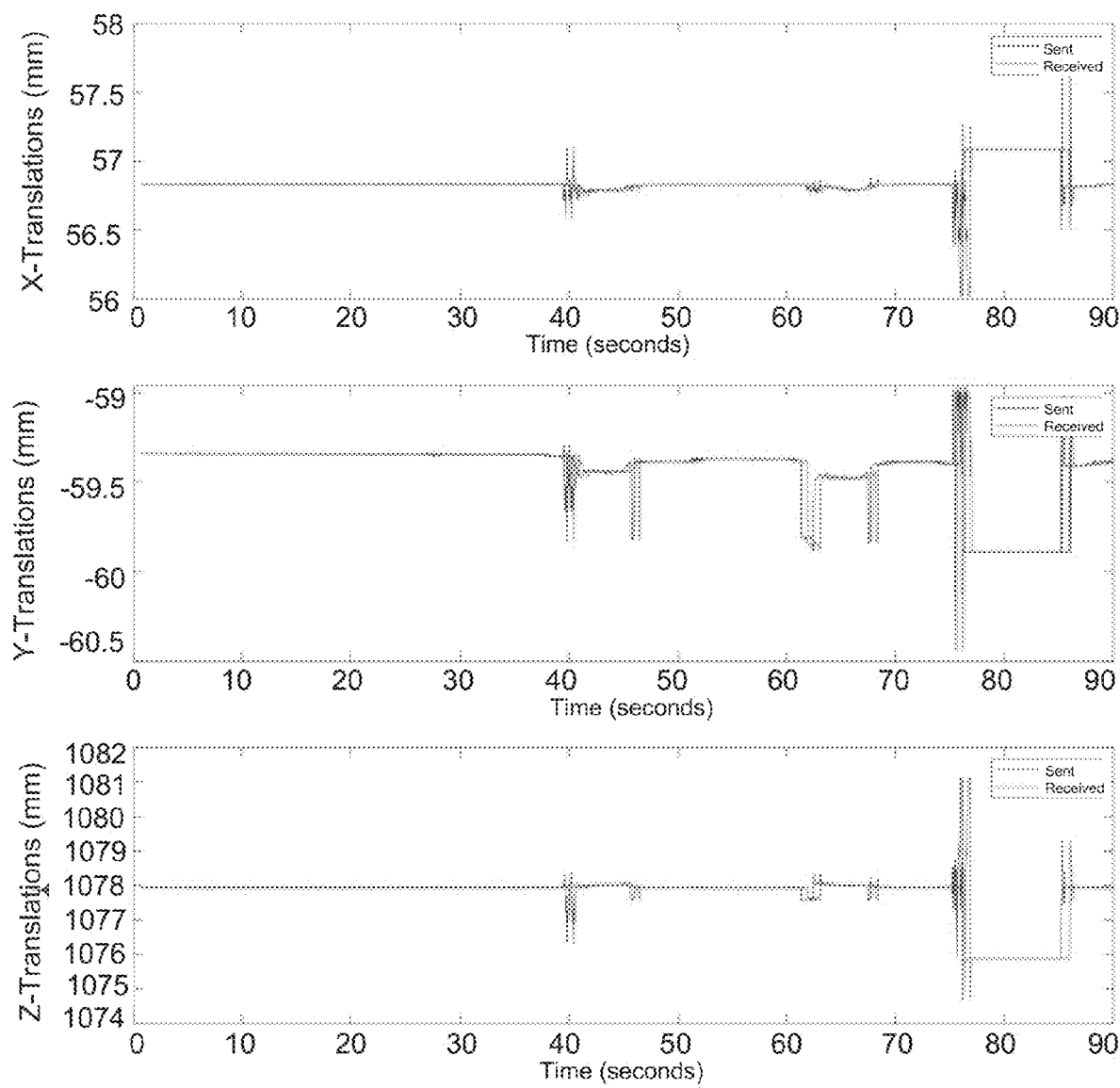

SYSTEM AND METHODS FOR TELE-COLLABORATION IN MINIMALLY INVASIVE SURGERIES

CROSS REFERENCE TO RELATED APPLICATION

The present application comprises a continuation-in-part application of International PCT Application PCT/QA2020/050005 filed Mar. 22, 2020, which claims priority to U.S. Provisional Application No. 62/822,482, filed on Mar. 22, 2019, the entire contents of which are being incorporated herein by reference.

BACKGROUND

Tele-medicine is playing an ever-increasing role in clinical practice with the aim to provide clinical healthcare from a distance ["Telemedicine in surgery," L. H. Eadie et al. The British Journal of Surgery 647-658, 2003]. It entails use of software/hardware technologies to share clinical information and edit it in real-time. An aspect of tele-medicine, when applied to surgical context, includes tele-mentoring, tele-conferencing, and tele-consulting during a surgery ["Telesurgery versus telemedicine in surgery—an overview," P Whitten el al. Surgical Technology International 68-72, 2004; International Foundation for Advancement of Surgical Telementoring https://www.telesurgeon.org]. As surgery has evolved from open to minimally invasive, the framework of these tele-collaboration technologies has remained the same. It still involves basic exchange of audio and annotated video messages and lacks augmentation of information pertaining to tool motion and tool-tissue interaction.

In an operating room setup of minimally invasive surgery (MIS), the surgeon operates on a patient using surgical instruments inserted through small incisions. These surgical instruments can either be manually-operated (such as laparoscopic instruments) or robotically-actuated. Along with instruments, a scope (camera) is also inserted inside the patient's body to visualize the interaction of surgical instruments' tooltips with the tissue. In the case of manual MIS, the surgeon directly controls the movements of the tooltips, whereas in the case of robotic MIS, the surgeon indirectly controls the movement of robotically-actuated tooltips via an interface on the console. In both cases of MIS, the surgical field exhibits the complex interaction of highly-articulated surgical instrument tooltips with the tissue to be operated.

With the current existing tele-mentoring technologies, the expert surgeon can assist the operating surgeon by providing guidance information in the form of either markings or hand gestures. However, this information is limited because of its two-dimensional and static nature. As a result, it is difficult for the operating surgeon to visualize, comprehend, and perform the required surgical tooltip movements. The notion of overlaying minimally invasive surgical instruments motion onto the surgical field is advantageous in mentoring scenarios. For example, augmented reality telementoring (ART) platform proposed by Vera et al. [Vera A M, Russo M, Mohsin A, Tsuda S. Augmented reality telementoring (ART) platform: a randomized controlled trial to assess the efficacy of a new surgical education technology. Surg Endosc. December 2014; 28(12):3467-72. doi:10.1007/s00464-014-3625-4] showed faster skill acquisition in laparoscopic suturing and knot-tying task. Preliminary studies conducted by Jarc et al. (using the ghost tool platform with da Vinci surgical system) demonstrated effectiveness for both trainees and proctors during robot-assisted dry-lab training exercises [Jarc A M, Shah S H, Adebar T, et al. Beyond 2D telestration: an evaluation of novel proctoring tools for robot-assisted minimally invasive surgery. J Robot Surg. June 2016; 10(2):103-9. doi:10.1007/s11701-016-0564-1], and robot-assisted tissue dissection and suturing tasks on a live porcine model [Jarc A M, Stanley A A, Clifford T, Gill I S, Hung A J. Proctors exploit three-dimensional ghost tools during clinical-like training scenarios: a preliminary study. World J Urol. June 2017; 35(6):957-965. doi:10.1007/s00345-016-1944-x].

In both academia ["Virtual interactive presence for real-time, long-distance surgical collaboration during complex microsurgical procedures," M. B. Shenai et al. Journal of Neurosurgery 277-284, 2014; "Virtual Interactive Presence in Global Surgical Education: International Collaboration through Augmented Reality," M. C. Davis et al. World Neurosurgery 103-111, 2016; "An augmented reality approach to surgical telementoring," T. Loescher et al. IEEE International Conference on Systems, Man and Cybernetics 2341-2346, 2014] and industry [Proximie, Boston, MA., http://www.proximie.com; VIPAAR, Birmingham, AL, https://helplightning.com; InTouchHealth, CA, https://www.intouchhealth.com; VisitOR1 from Karl Storz, https://www.karlstorz.com/bd/en/visitor1-telemedicine-evolves-in-toremote-presence.htm], augmented reality based solutions have been developed to provide tele-collaboration during a surgery between a remote and a local surgeon. These solutions include interfaces to share the live video feed of the surgical view over a network, perform screen markings, and display augmented hands' gestures of remote surgeon. They allow a remote surgeon to virtually put his/her hand in the surgical view and point out different anatomical structures, incision positions, and surgical instrument placements. Although these solutions are sufficient for open surgeries, a more sophisticated mechanism is required for minimally invasive surgeries (either manual-laparoscopic or robotic) which involve complex interaction between the highly-articulated surgical instrument tooltips and tissues in the surgical field. During a Minimally Invasive Surgery (MIS), by just analyzing the hand gestures or markings provided by a remote surgeon, it is difficult for the local surgeon to visualize, comprehend, and perform the required tooltip movements.

SUMMARY

In a general embodiment, the present disclosure provides a method comprising: connecting a local workstation and a remote workstation; providing to at least one of the local workstation or the remote workstation at least one of an instrument state or a scope state; providing at least one of a trocar, a trocar tracking frame attached to the trocar, a scope, or a scope tracking frame attached to the scope; and continuously updating at least one of a surgical state, a tooltip pose, data to be communicated over network, or a rendered object on a visualization screen in each of the local and remote workstations.

In one embodiment, the method comprises providing the trocar and further comprising providing a label indicating a position of the trocar.

In one embodiment, the method comprises mapping at least one of an instrument type or a human computer interface to the label.

In one embodiment, the method comprises mapping the human computer interface to the label.

In one embodiment, the method comprises interacting with the human computer interface and updating the tooltip pose of a rendered augmented tool on both the local and remote workstations.

In one embodiment, the instrument state comprises a list of instruments to be used.

In one embodiment, the scope state comprises at least one of the scope's field of view (FOV), the scope's angulation, and transformation between $M_{Scope(t)}$ and $M_{ScopeCamera}(t)$, wherein $M_{Scope}(t)$ represents a pose of the scope tracking frame attached to the scope in form of 4×4 homogenous transformation matrix for time instant "t," and $M_{ScopeCamera}(t)$ represents a pose of scope camera is represented by 4×4 homogenous transformation matrix at time instant "t."

In one embodiment, the at least one of the instrument state and the scope state is shared by both the local workstation and the remote workstation.

In another general embodiment, the present disclosure provides a system comprising a local system comprising an input/output device selected from the group consisting of a microphone, a speaker, a first visualization screen, and combinations thereof, a scope system comprising at least one of a scope, a camera, a camera system, a scope's tracking frame, and combinations thereof, an optical tracking system, a trocar system comprising at least one of a trocar, a trocar's tracking frame, and combinations thereof; and a remote system connected to the operating room system via a network, the remote system comprising a human computer interface system comprising at least one of a camera, a sensor, a user interface, and combinations thereof, a second visualization screen.

In one embodiment, the local system further comprises an operating instrument.

In another general embodiment, the present disclosure provides a method for surgical collaboration and training, the method comprising: transforming a hand gesture of a first user into a virtual tooltip movement; and superimposing the virtual tooltip movement on a second user's view of a surgical field.

In one embodiment, transforming the hand gesture of the first user into the virtual tooltip movement can comprise extracting a position of at least one optical marker attached to a grasper in the first user's hand; triangulating the position into a position of the virtual tooltip.

In one embodiment, the present disclosure can include receiving a video frame; and extracting an actual tooltip from the video frame to form the virtual tooltip; and computing a position of the actual tooltip.

In one embodiment, the present disclosure can include calibrating the position of the virtual tooltip from the hand gesture with the actual tooltip from the video stream; and rendering a complete virtual tool if the actual tooltip and the virtual tooltip are aligned, or rendering only the virtual tooltip if the actual tooltip and the virtual tooltip are not aligned.

In one embodiment, the present disclosure can include rendering an augmented-reality scene on a visualization screen.

In one embodiment, the present disclosure can include rendering the virtual tooltip movement generated by the first user along with a video stream from a scope's camera on a visualization screen.

In one embodiment, the present disclosure can include transmitting a live video stream from the first user's workstation to the second user's workstation over a network.

In one embodiment, the second user can be performing a minimally invasive surgery.

In another general embodiment, the present disclosure also provides a system for surgical collaboration and training. The system can comprise a first computing system comprising first I/O devices configured for a first user to receive and send information; a second computing system comprising second I/O devices for a second user to receive and send information, wherein the first and second I/O devices are each selected from the group consisting of an infrared camera configured to capture the second user's hand gestures holding a grasper, the grasper, a scope configured to capture a video of a surgical field at the first user's end, a first visualization screen configured to display the video of the surgical field, a second visualization screen configured to display an augmented surgical field, and combinations thereof; a module configured to operate on at last one of the first or second computing systems, wherein the module is selected from the group consisting of a video processing module configured to receive a video frame from a network module, extract an actual tooltip from the video frame, and compute a position of the tooltip, a control logic module configured to take a first input from the video processing module and a reconstruction module and provide a second input to an augmentation module on graphical rendering; an augmentation module configured to render an augmented-reality scene on the second visualization screen, the reconstruction module configured to transform the second user's hand gestures into movements of a virtual tooltip, the network module configured to exchange data over a network connecting the first and second computing system, and combinations thereof.

In one embodiment, the second I/O devices can comprise the infrared camera, and the system further comprises the grasper.

In one embodiment, the grasper can comprise a pinching member configured to constrain a motion of the second user's hand holding the grasper and at least one optical marker configured to trace the motion of the second user's hand and at least one of opening or closing of the grasper in the infrared camera.

In one embodiment, the pinching member can be configured to constrain a motion of the second user's index finger and thumb with respect to each other.

In one embodiment, the reconstruction module can be configured to transform the second user's hand gestures into movements of the virtual tooltip by extracting a position of the at least one optical marker attached to the grasper and triangulating the positions into a position of the virtual tooltip.

In one embodiment, the control logic module can be configured to calibrate the position of the virtual tooltip from the second user's hand gestures with an actual tooltip from the video stream.

In one embodiment, the augmentation module can be configured to receive an input in a form of video frame from the network module and decision to render a tooltip or complete tool from the control logic module.

In one embodiment, the augmentation module can be configured to, based on the input, render the augmented reality scene consisting of three-dimensional computer graphics rendered on the video stream.

In one embodiment, the augmentation module can comprise an inverse kinematics sub-module configured to compute the position of the virtual tooltip.

In one embodiment, the position of the virtual tooltip can comprise at least one of a degree-of-freedoms or a base frame.

In another general embodiment, the present disclosure also provides a method comprising receiving a video frame including actual tooltip, extracting the actual tooltip from the video frame, and computing a position of the actual tooltip, by a video processing module of a computing system comprising at least one processor and a data storage device in communication with the at least one processor; receiving an input from the video processing module and a reconstruction module and providing the input to an augmentation module on graphical rendering, by a control logic module of the computing system; rendering, by the augmentation module of the computing system, an augmented-reality scene on a first visualization screen; transforming a user's hand gestures into movements of a virtual tooltip, by the reconstruction module of the computing system; exchanging data, by a network module of the computing system, over a network.

In one embodiment, the method can further comprise capturing, by an infrared camera, the user's hand gestures holding the actual tooltip; capturing, by a scope, a video of a visual field; and displaying the video of the surgical field on a first visualization screen.

Additional features and advantages are described herein, and will be apparent from the following Detailed Description and the figures.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 11 shows the registration window, and FIG. 12 shows the augmentation window.

FIGS. 13A and 13B illustrate the sequence of steps performed by the operating surgeon and the mentor according to some aspects of the present disclosure.

DETAILED DESCRIPTION

Figure 1:
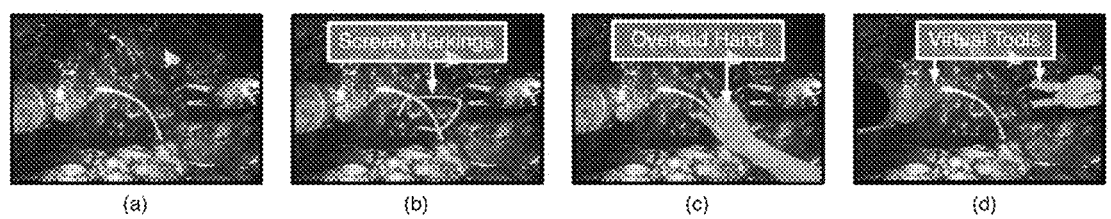
FIG. 1 shows (a) view of the surgical field observed by a local surgeon in minimally invasive surgery comprising of tooltips and tissue to be operated; (b) assistance provided by remote surgeon to local surgeon in form of augmented screen markings using existing technologies; (c) assistance provided by remote surgeon to local surgeon in form of overlaid hand motions using existing technologies; and (d) assistance provided by remote surgeon to local surgeon in form of enhanced three-dimensional, dynamic, virtual tools using proposed technology.

The present disclosure relates generally to tele-collaboration technology. More specifically, the present disclosure provides, in an embodiment, a tele-collaboration technology for MIS that would address clinical problems and unmet needs.

In an MIS operating room setting, for example, where an experienced surgeon is mentoring a novice surgeon, the experienced surgeon frequently takes control to demonstrate a complex surgical-step to the novice surgeon. The novice surgeon either steps down from the console (in case of robotic surgery) or hands over the control of instruments (in case of manual laparoscopic surgery) and observes the procedure on a secondary screen. This switching between surgeons during the procedure is inevitable as there is no other way to demonstrate the exact movements of the tooltips required to interact with the tissue. The inventors have recognized that this generates a need of a tele-collaboration technology that can allow the experienced surgeon to virtually demonstrate the exact tool-tissue interactions required during an MIS procedure while the novice surgeon is still in control of surgical instruments.

An MIS has high complication rates unless the procedure is performed by an experienced specialist surgeon. To gain experience in usage of new surgical instruments or new surgical technique for an MIS, the surgeon has to go through a learning curve. It may require a local surgeon to travel to get trained or invite a specialist surgeon to the local hospital to perform multiple surgeries a day continuously for at least a few days. This imposes a burden in terms of time (scheduling patients only when the specialist surgeon is available) and logistics (such as travel, stay, and cost per day). A tele-collaboration technology for an MIS would overcome the associated problems as both the local and specialist surgeons need not be present in the same place. It is also worth noting that in developing economies and small countries, a regional shortage of a surgical sub-specialty may arise within a country due to uncontrollable geo-political factors. An imbalance of surgeons' inflow and outflow may affect surgical services. In such cases, tele-mentoring technology for MIS could facilitate surgical knowledge transfer across geographical boundaries.

A regional shortage of a sub-specialty may arise within a country due to uncontrollable geo-political factors. An imbalance of surgeons' inflow and outflow may affect surgical services. In such cases, a tele-collaboration technology would facilitate surgical knowledge transfer across geographical boundaries.

The present disclosure provides immersive, augmented reality-based, enabling technology for tele-collaboration between a local surgeon and a remote surgeon during an MIS according to an embodiment. The technology would provide realistic visual-cues to the local surgeon for the required movement of an actuated, high degree-of-freedom surgical tool during an MIS.

In an operating room setting for a MIS, the local surgeon operates on a patient using surgical instruments inserted through small incision. These surgical instruments can either be manual-operated (such as laparoscopic instruments) or robotically-actuated (such as robotic instruments). Along with instruments, a scope (camera) is also inserted inside the patient's body to visualize the interaction of surgical instruments' tooltips with the tissue. In a manual MIS, the surgeon directly controls the movements of the tooltips, whereas in a robot-assisted MIS, the surgeon indirectly controls the movement of robotically-actuated tooltips via an interface on the console. In both MIS, the surgical field exhibits the complex interaction of highly-articulated surgical instrument tooltips with the tissue to be operated.

For example, in the view of the surgical field shown in FIG. 1*a*, the local surgeon is suturing the tissue. Even a regular surgical task, such as of suturing a tissue, is highly complex in nature as it involves three-dimensional interaction and precise motion of tooltips with-respect-to tissue being sutured. With existing tele-collaboration technologies, the remote surgeon can assist the local surgeon by providing guidance information in the form of markings (FIG. 1*b*) or hand gestures (FIG. 1*c*). However, this guidance information is limited because of its two-dimensional and static nature. As a result, it is difficult for the local surgeon to visualize, comprehend, and perform the required tooltip movements.

The present technology overcomes this limitation by enabling the remote surgeon to demonstrate the exact tool movement required in form of an augmented dynamic virtual tool (FIG. 1*d*) according to an embodiment.

Figure 2:
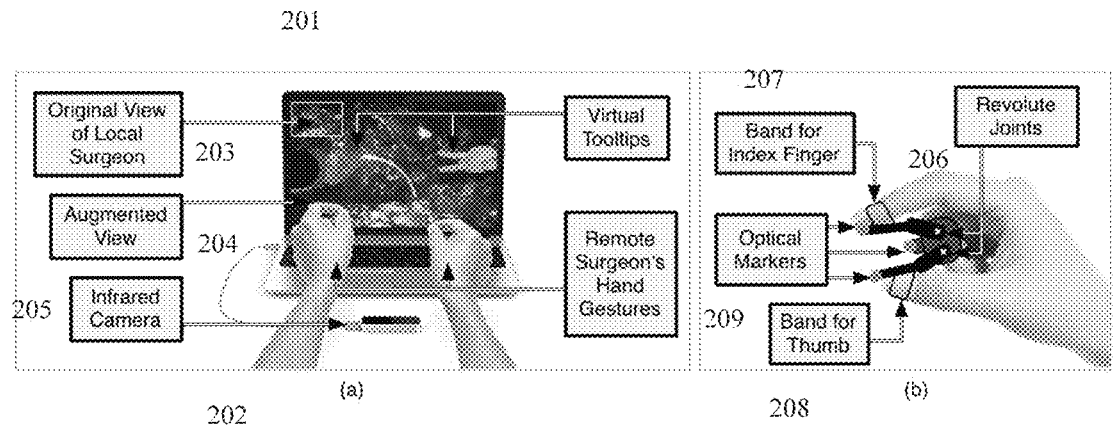
FIG. 2 shows (a) setup at remote surgeon's end and (b) a custom-build low-cost grasper to be used by the remote surgeon to control the motion of virtual tooltips, according to some aspects of the present disclosure.

The remote surgeon will get connected with the operating room for tele-collaboration via laptop over network and an infrared camera. FIG. 2*a* shows a setup at remote surgeon's end comprising of a laptop and an infrared camera. The infrared camera can be a low-cost compact device with infra-red LEDs (such as https://www.leapmotion.com) to capture the hand-gestures for control of the virtual tool (FIG. 2*a*).

The laptop 201 is connected with the operating room over a network. The remote surgeon 202 is able to see the original view 203, as seen by local surgeon, and generates an augmented view 204, which includes the virtual tooltips movements. The infrared camera 205 captures the remote surgeon's hand-gestures and generates the movements of the virtual tooltips. The augmented view 204 is sent back to local surgeon over the network for assistance.

FIG. 2*b* shows the custom-build low-cost grasper 206 to be used by the remote surgeon 202 to control the motion of virtual tooltips. The graspers 206 can have pinching mechanism 207, 208 to constrain the motion of the remote surgeon's index finger and thumb with respect to each other. The graspers can also have attached optical markers 209 to trace the motion as well as opening/closing of the grasper in infrared cameras. The positions of optical markers 209 attached on grasper 206 can be extracted and transformed to movements and opening/closing of the virtual tooltips.

Figure 3:
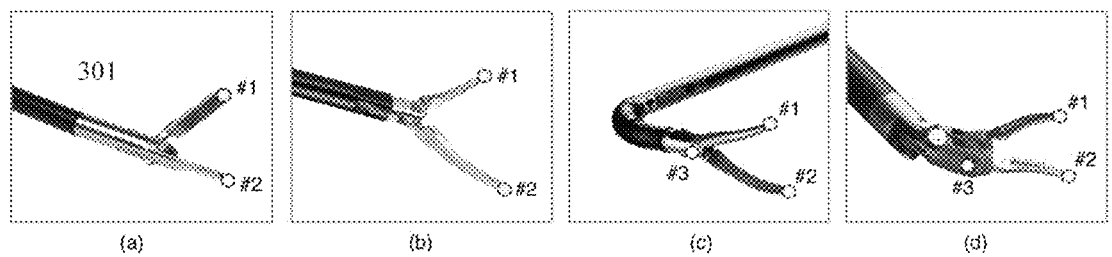
FIG. 3 illustrates the mapping between optical makers and corresponding points on the tooltips for (a) a single-action manual tool, (b) a double-action manual tool, (c) a flexible double-action manual tool, and (d) a double-action robotic tool, according to some aspects of the present disclosure.

The motion and opening/closing of the grasper can be mapped to the virtual tool's tooltips. FIG. 3 shows a set of surgical tooltips typically used in minimally invasive surgery. The motion of the optical markers 301 on the graspers can be mapped to the virtual models of these surgical tooltips. The figures illustrates the mapping between optical makers and corresponding points (#1, #2, #3) on the tooltips for (a) a single-action manual tool, (b) a double-action manual tool, (c) a flexible double-action manual tool, and (d) a double-action robotic tool.

Architecture of Tele-Mentoring Framework

Figure 4A:
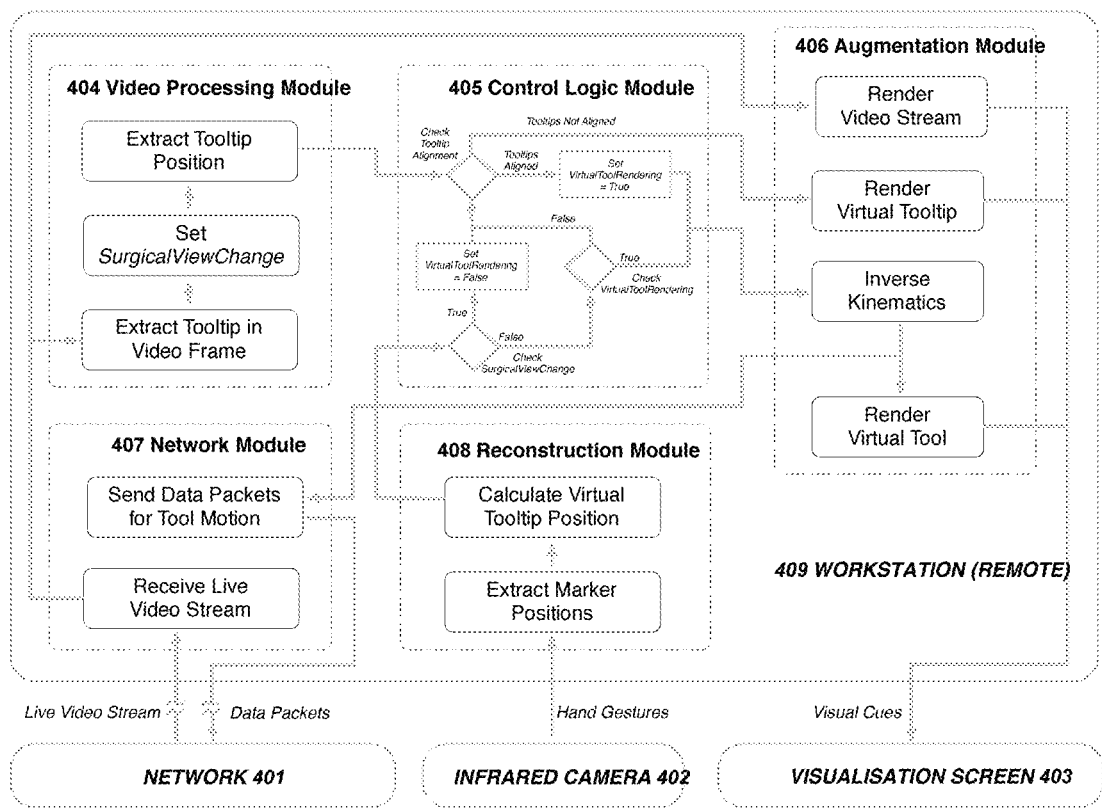
FIG. 4A shows an example system architecture at remote surgeon's end illustrating the interaction among the hardware (Workstation, Network, Infrared Camera, and Visualization Screen) and software (Video Processing, Control Logic, Augmentation, Network, and Reconstruction Modules) according to some aspects of the present disclosure.
Figure 4B:
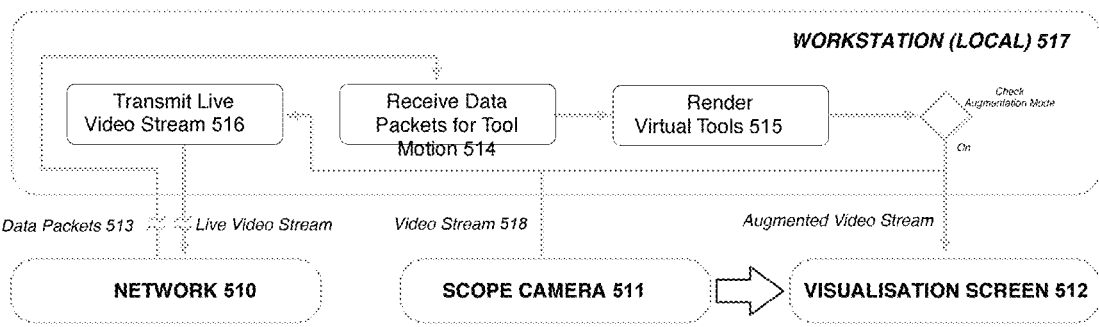
FIG. 4B shows an example system architecture at remote surgeon's end illustrating the interaction of Scope Camera, Visualization Screen, Network with software running on the local workstation according to some aspects of the present disclosure.

An example system architecture of the present disclosure, in an embodiment, is presented in FIGS. 4A and 4B. FIG. 4A shows an example system architecture at the remote surgeon's end illustrating the interaction among the hardware (Workstation, Network, Infrared Camera, and Visualization Screen) and software (Video Processing, Control Logic, Augmentation, Network, and Reconstruction Modules). FIG. 4B shows an example system architecture at the local surgeon's end illustrating the interaction of Scope Camera, Visualization Screen, Network with software running on local workstation.

According to some aspects of the present disclosure, the system can include software modules running of a local and a remote workstation, interfacing with I/O devices, and continuously communicating over a network. The remote workstation can be a laptop whereas the local workstation would be a desktop with audio-video PCI cards and cables for bifurcating the video stream. The I/O device can include an infrared camera to capture the remote surgeon's hand gestures via the custom build grasper, a scope to capture the video of the surgical field at local surgeon's end, and visualization screens to view the augmented surgical field.

On the remote surgeon's workstation (FIG. 4A), different software modules can be running as parallel threads continuously interacting with each other. The Reconstruction Module 408 transforms the hand gestures of the remote surgeon into movements of virtual tooltips by extracting the positions of the optical markers attached to the grasper and triangulating it into the position of the virtual tooltip. At the same time, the Video Processing Module 404 can receive a video frame from Network Module, extract the actual tooltip from the video frame, and compute its position. It can also set a Boolean variable SurgicalViewChange to true or false, depending whether two successive frames are same or not.

The Control Logic Module 405 takes input from Video Processing Module 504 and Reconstruction Module 408 and provides input to Augmentation Module 506 on graphical rendering. This module calibrates the position of virtual tooltip from hand gestures with actual tooltip from the video stream. If both the tooltips are aligned, it enables rendering of complete virtual tool, otherwise it enables rendering of just virtual tooltip. The Boolean variable VirtualToolRendering can enable faster rendering of the virtual tool by bypassing the computationally expensive check of tool alignment in Control Logic Module 405.

The Augmentation Module 406 is responsible for rendering the augmented-reality scene on the visualization screen. It receives input in form of video frame from Network Module 407 and decision to render tooltip or complete tool from Control Logic Module 405. Based on the input, the module renders the augmented reality scene consisting of three-dimensional computer graphics rendered on a video stream. It also has inverse kinematics sub-module to compute the position (in terms of degree-of-freedoms and base frame) of the virtual tool from tooltip position.

The output of this submodule is also sent to Network Module 407. The Network Module 407 is responsible for data exchange over the network and has two functions. First, it receives live video stream over the network from the local surgeon's workstation, convert it into frames, and provides it to Video Processing Module 404 and Augmentation Module 406. Second, it receives degree-of-freedom from Augmentation Module 406, compresses it into data-packets and send it over the network to local surgeon's workstation.

At the local surgeon workstation (FIG. 4B), these data packets 513 are received 514 and the tool motion is extracted for rendering 515. If augmentation mode is on, the virtual tool movement generated by the remote surgeon is rendered along with video stream from the scope's camera on the local surgeon's visualization screen. The local surgeon workstation also transmits the live video stream 516 to the remote surgeon workstation over the network 510. The local workstation 517 is in the operating room, and the video stream 518 from the scope camera 511 is bifurcated to the workstation 517, when tele-collaboration is required by the surgeon.

Figure 5A:
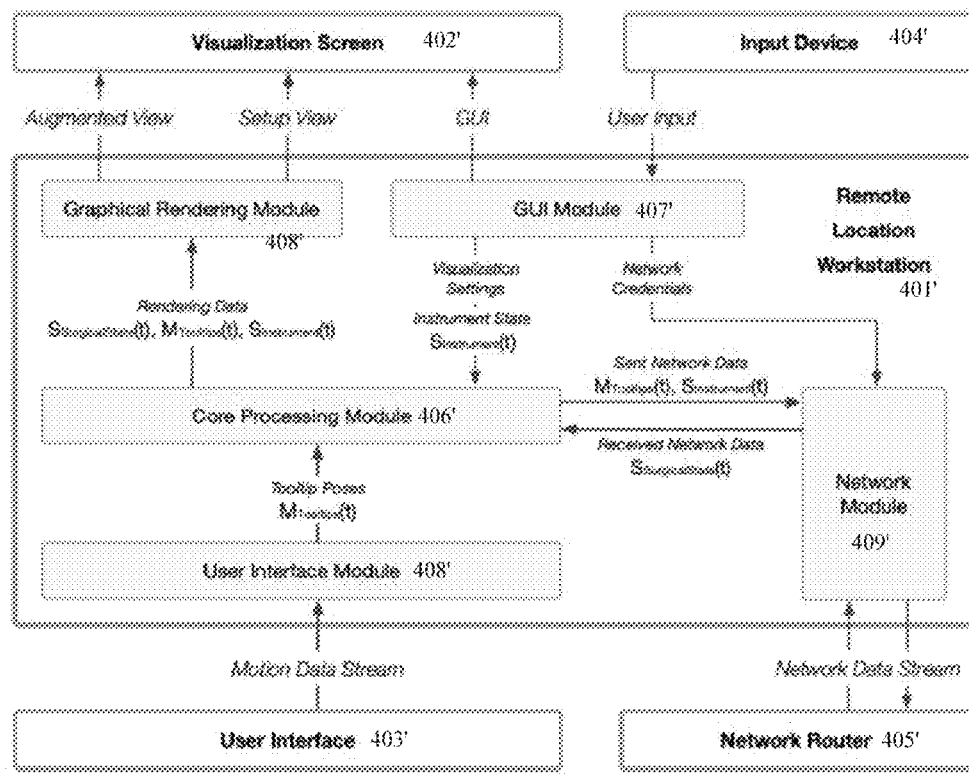
FIG. 5A shows a further embodiment of the system architecture at remote surgeon's end illustrating the interaction among the hardware and software according to some aspects of the present disclosure.
Figure 5B:
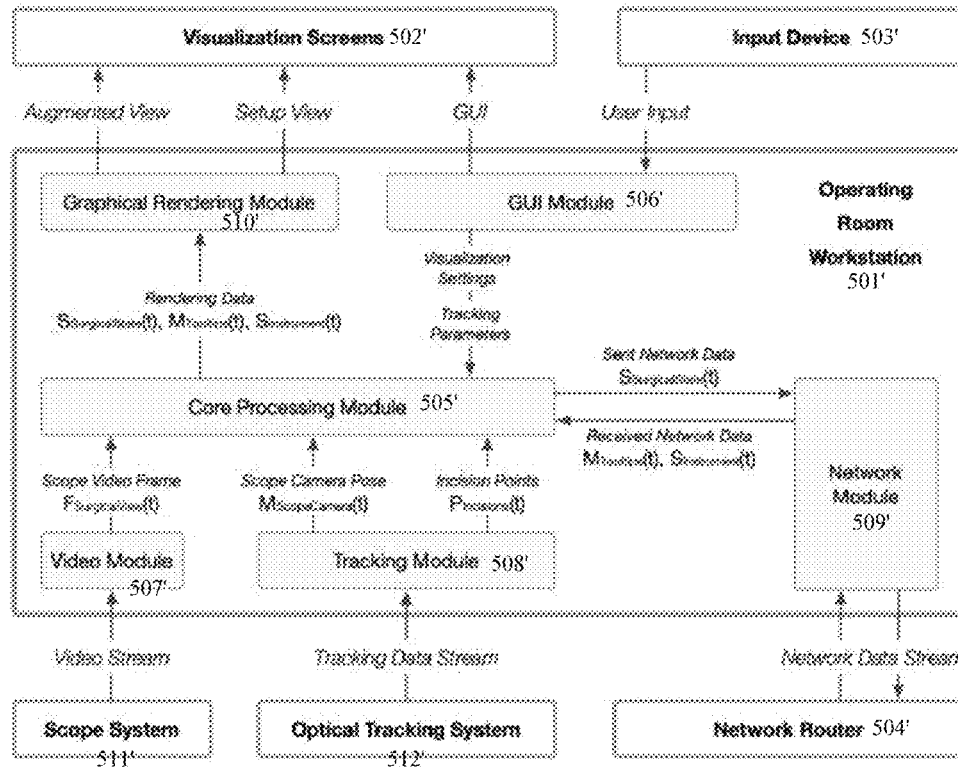
FIG. 5B shows a further embodiment of the system architecture at remote surgeon's end illustrating the interaction of hardware and software according to some aspects of the present disclosure.

FIGS. 5A and 5B illustrate a further example embodiment of system architecture of the present disclosure. Referring to FIG. 5A, the example remote location setup consists of a remote location workstation 401', visualization screens 402', a user-interface 403', an input device 404', and a network router 405'. The remote location workstation 401' includes five software modules interfacing with the hardware units, processing the data, and continuously communicating with each other.

The Core Processing Module 406' acts as a central core for processing data at the remote location workstation. The module 406' receives data from the Graphical User Interface (GUI) Module 407', User Interface Module 408', and Network Module 409' and sends data to Graphical Rendering Module 410' and Network Module 409'.

The User Interface Module 408' fetches the motion data stream from the user interfaces 403', processes it and converts it into the poses of augmented tooltips $M_{Tooltips}(t)$. The transformation of $M_{Tooltips}(t)$ causes the augmented surgical instruments to move in the rendered view of the surgical setup (FIGS. 13A and 13B) and augmented view of the surgical field (FIGS. 14A and 14B).

The graphical rendering module fetches the information from the core processing module and renders it on the visualization screen.

The GUI Module 407' is used to establish a connection with the operating room workstation, alter the visualization setting, and set the instrument state. It allows the user to connect to the operating room workstation by entering the IP address, map virtual tools to incision points for left/right hand tool movements, and display the status of the operating room workstation.

The Network Module 409' receives the network data stream from the operating room workstation, processes it, and extracts $S_{SurgicalState}(t)$ from it. In parallel, the Network Module 409' also sends poses of augmented tooltips $M_{Tooltips}(t)$ and instrument state $S_{SurgicalState}(t)$ to the operating room workstation.

Referring to FIG. 5B, the operating room setup includes an operating room workstation 501', visualization screens 502', an input device 503', and a network router 504'. The operating room workstation 501' includes six software modules interfacing with the hardware units, processing the data, and continuously communicating with each other.

The Core Processing Module 505' acts as a central core for processing data at the operating room workstation 501'. The Core Processing Module 505' receives data from the Graphical User Interface (GUI) Module 506', the Video Module 507', the Tracking Module 508', the Network Module 509', and sends data to the Graphical Rendering Module 510' and the Network Module 509'.

The Video Module 510' receives video stream of the surgical field from the scope system 511', processes it frame-by-frame and sends the video frames to the Core Processing Module 505'.

The Tracking Module 508' processes data related to the scope and trocars. Tracking frames with unique arrangement of retroreflective markers are attached to the scope and trocars. The optical tracking system 512' continuously sense the poses (position and orientation) of the tracking frames and sends the tracking data stream to the Tracking module 508'. The Tracking Module 508' processes the stream and computes the pose of the scope camera and the positions of the incision points (shown in FIG. 12). The scope camera's pose at the time instant 't' is represented by a 4×4 homogenous transformation matrix $M_{ScopeCamera}(t)$. Whereas, the positions of the incision points are stored in a tuple $P_{Incisions}(t)$, where each element represents an incision point $P_{Incisions}[i](t)$, (where i=number of incisions). $M_{ScopeCamera}(t)$ and $P_{Incisions}(t)$ are measured with respect to the coordinate system of the optical tracking system inside the operating room and are fed to the Core Processing Module 505'.

The GUI Module 506' is used to alter the visualization setting and to set the tracking parameters for the tracking module. It allows the user to add/delete incision points, set deflection angle for angulated scope, toggle visualization of augmented instruments, display instruments selected by remote surgeon, and status of the operating room workstation.

Figure 12:
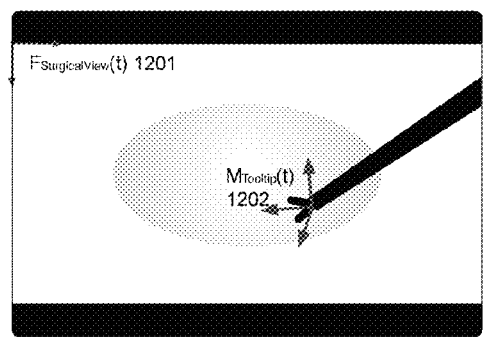

The Network Module 509' enables communication with the remote location workstation 401'. The video frame of the surgical view, pose of the scope camera, and coordinates of the incisions points together define the surgical state $S_{SurgicalState}(t)=[F_{SurgicalView}(t), M_{ScopeCamera}(t), P_{Incisions}(t)]$ at time instant 't'. The surgical state $S_{SurgicalState}(t)$ is sent by the Core Processing Module 505' to the Network Module 509', which further passes it as a network data stream to the remote location's workstation 401'. The Network Module 509' also receives the poses of augmented tooltips $M_{Tooltips}(t)$ and instrument state $S_{Instrument}(t)$ from the remote workstation. $M_{Tooltips}(t)$ is represented by a tuple $[M_{Tooltips[1]}(t), M_{Tooltips[2]}(t)]$ corresponding to left and right tool motion. $M_{Tooltip[i]}(t)$ represents a coordinate frame in form of 4×4 homogenous transformation matrix attached to the tooltip of the augmented surgical instrument. The transformation of $M_{Tooltip[i]}(t)$ causes the augmented surgical instrument to move in the virtual space. The instrument state $S_{Instrument}(t)$ stores: (a) surgical instrument types used in the surgery, (b) labels of the incision point, and (c) mapping between surgical instrument type to an incision point label and left- or right-hand interface to an incision point label (as shown in FIG. 12). The mapping inside $S_{Instrument}(t)$ data is used by the graphical rendering module during rendering.

The Graphical Rendering Module 510' renders the information fetched from the Core Processing Module 505' onto the visualization screen 502'. The data comprising of $S_{SurgicalState}(t)$, $M_{Tooltips}(t)$, and $S_{Instrument}(t)$ is rendered in two windows displaying view of the surgical setup (FIGS. 13A and 13B) and augmented view of the surgical field (FIGS. 14A and 14B). The setup view renders pose of tracking frames, pose of the scope camera, location of the incision points (along with labels), the frustum of the surgical view (along with the updated surgical view frame), and pose of the augmented tools selected. The augmented view displays the surgical view $F_{SurgicalView}(t)$ in the complete window along with augmented tools when selected by the remote surgeon.

Figure 6A:
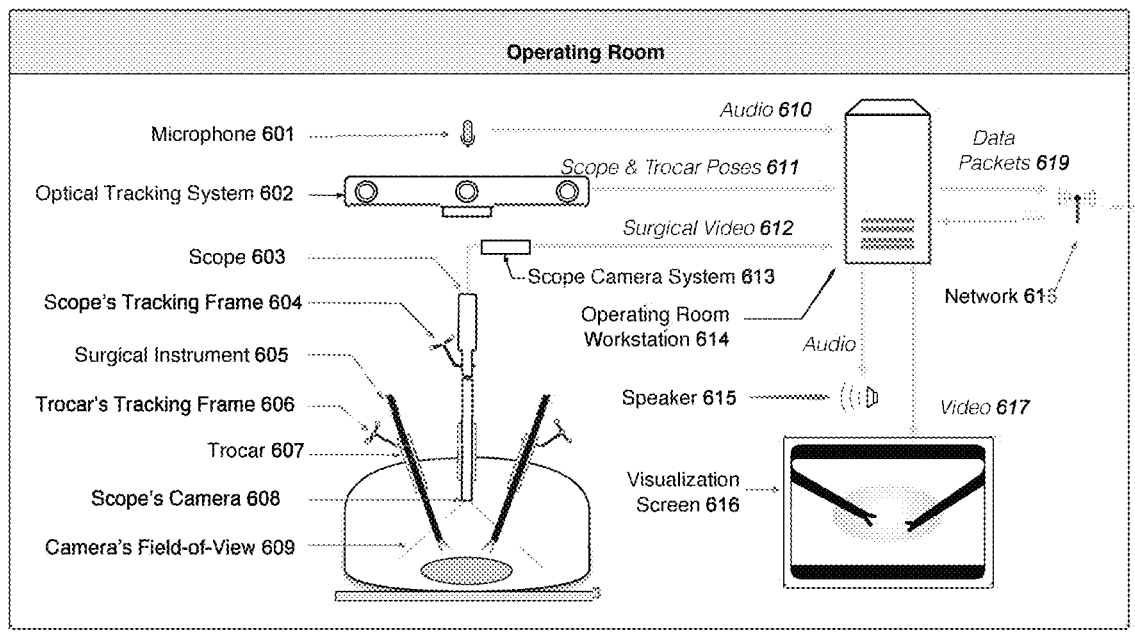
FIG. 6A shows an example operation room system architecture according to some aspects of the present disclosure.

FIG. 6A shows an example operation room system architecture illustrating the flow of information among the hardware components 601-616 physically located in the operating room. The operating room hardware components may comprise operating room workstation 614, optical tracking system 602, visualization screens 616, scope camera system 613, tracking frames 604 to be used with optical tracking system 602, and/or audio I/O devices 601, 610, 612, 615.

Figure 6B:
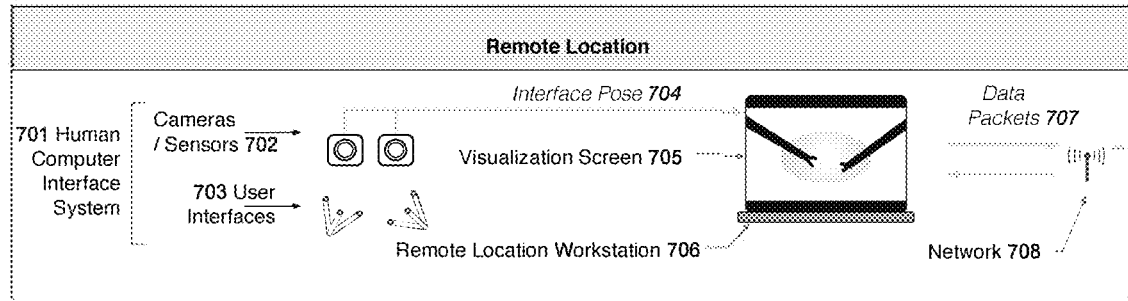
FIG. 6B shows an example remote location system architecture according to some aspects of the present disclosure.

FIG. 6B shows an example remote location system architecture illustrating the flow of information among the hardware components 701-706 physically located at the remote location. The remote location hardware components may comprise remote location workstation 706, human computer interface system 701, visualization screen 705, human computer interfaces 703, and/or audio I/O devices 702, 705.

A network connection 618,708 is present connecting the workstations inside operating room and remote location. The software modules run on operating room workstation and remote location workstation, interfacing with other hardware components and continuously communicating over the network.

Figure 7A:
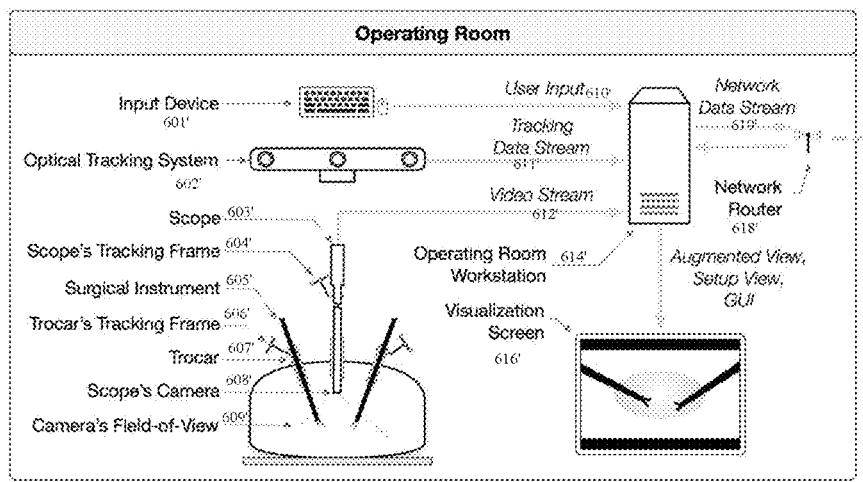
FIG. 7A shows a further example operation room system architecture according to some aspects of the present disclosure.
Figure 7B:
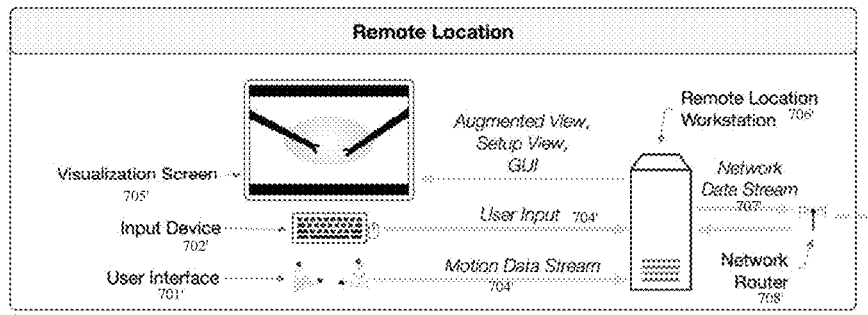
FIG. 7B shows a further example remote location system architecture according to some aspects of the present disclosure.
Figure 8:
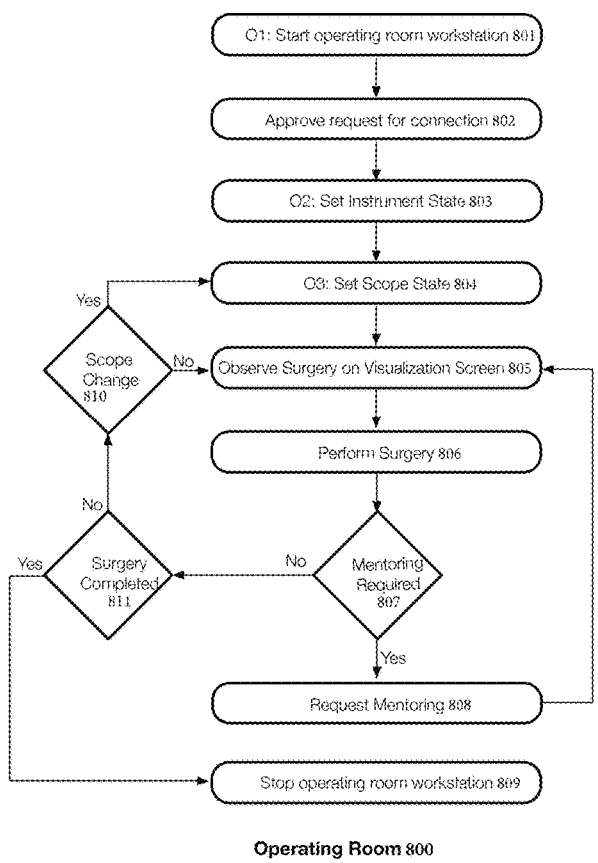
FIG. 8 shows an example workflow inside the operating room according to some aspects of the present disclosure.
Figure 9:
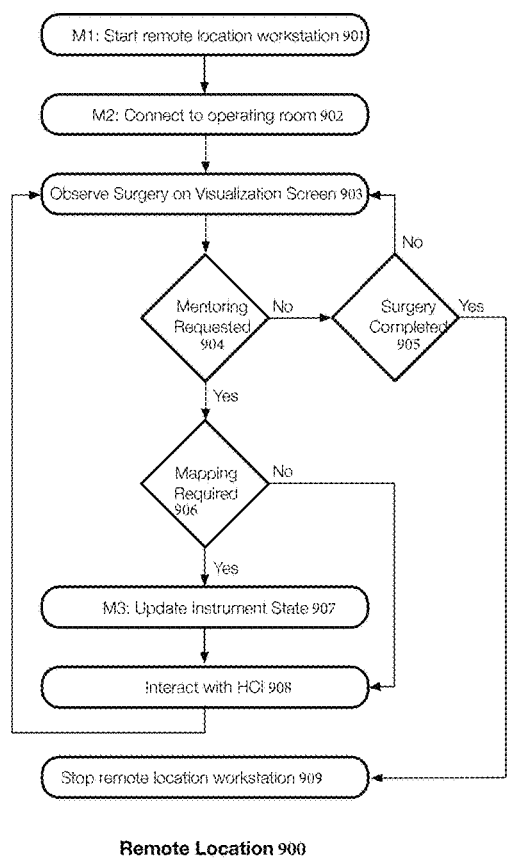
FIG. 9 shows an example workflow at the remote location according to some aspects of the present disclosure.

FIGS. 7A and 7B show further example operation room and remote location system architecture illustrating the flow of information among hardware components 601'-616' and 701'-706'. A network connection 618', 708' connects the workstations inside the operating room and remote locations. The architecture of FIGS. 7A and 7B are similar to the architecture of FIGS. 6A and 6B, and demonstrate the use of additional input devices. FIG. 8 shows an example workflow inside the operating room according to some aspects of the present disclosure. FIG. 9 shows an example workflow at the remote location according to some aspects of the present disclosure.

In further embodiments, every interaction with the hardware unit to process data is performed by a task-dedicated parallel-running thread. The multi-threaded architecture streamlines the flow of processed data internally as well as externally with the hardware units and the network. Table 1 provides an exemplary list of processed data and the flow of each set of data in the operating room and at the remote location.

TABLE 1

Data processed and shared by the architecture of the tele-mentoring prototype

| Data | Description of the processed data |
|---|---|
| Scope Camera Pose $M_{ScopeCamera}(t)$ | A 4 × 4 homogenous transformation matrix measured with respect to optical tracking system and representing the position and orientation of the scope's camera at time instant 't'. The tracking thread processes the tracking data stream acquired from the optical tracking system to extract the scope camera poses. |
| Scope Video Frame $F_{SurgicalView}(t)$ | A frame of the operating field video at time instant 't'. The video stream acquired from the scope system is processed by video processing thread to extract the video frame. It also is combines the scope camera pose with scope video frame. |

TABLE 1-continued

Data processed and shared by the architecture of the tele-mentoring prototype

| Data | Description of the processed data |
| --- | --- |
| Incision Points $P_{Incisions}(t)$ | A tuple storing the positions of the incision points at time instant 't' and measured with respect to optical tracking system. Each element of the tuple represents an incision point. The tracking thread processes the tracking data stream acquired from the optical tracking system extract the incision points. |
| Tooltip Poses $M_{Tooltips}(t)$ | A tuple storing left and right tooltip poses at time instant 't'. Each element represents a co-ordinate frame in form of 4 × 4 homogenous transformation matrix attached to the tooltip of the augmented surgical instrument. The tool motion data stream acquired from the user interface is processed by the interfacing thread to extract tooltip poses. |
| Visual Rendering Data | The data comprises of scope camera pose, scope video frame, incision points, tooltip poses, and system parameters. It is sent to the visual rendering thread, which uses the data to render scenes on visualization screen. The primary scene contains the augmented operative filed with overlaid virtual surgical tools. The secondary scene gives a 3D view of the surgical setup assisting mentor to understand the configuration of incision points during surgery. |
| System Parameters | The system parameters at operating room workstation assists to set the labels to the incision points for intraoperative tracking, set the angulation angle of the scope, and accept the connection from the remote location. The system parameters at remote location workstation assists to set the network connection with the operating room, and map virtual surgical tooltips to the incision points for left/right hand tool movements. |

The relative flows of the data sets in the operating room and at the remote location are governed by the core-processing thread described in Algorithm 1 and Algorithm 2, respectively.

ALGORITHM 1

Core Processing Thread (Operating Room)

1: while (tele-mentoring)
2: Fetch $M_{ScopeCamera}(t)$ & $F_{SurgicalView}(t)$ from video processing thread
3: Fetch $P_{Incisions}(t)$ from tracking thread
4: Send $M_{ScopeCamera}(t)$ and $F_{SurgicalView}(t)$ to network video thread
5: Send $P_{Incisions}(t)$ to network data thread
6: Fetch $M_{Tooltips}(t)$ from network data thread
7: Send Visual Rendering Data to visual rendering thread
8: end-while

ALGORITHM 2

Core Processing Thread (Remote Location)

1: while (tele-mentoring)
2 Fetch $M_{Tooltips}(t)$ from interfacing thread
3: Send $M_{Tooltips}(t)$ to network data thread
4: Fetch $M_{ScopeCamera}(t)$ & $F_{SurgicalView}(t)$ from network video thread
5: Fetch $P_{Incisions}(t)$ from network data thread
6: Send Visual Rendering Data to visual rendering thread
7: end-while Workflow of Tele-Mentoring Framework As illustrated in FIGS. 8-9, before the start of the surgery, the operating surgeon starts the workstation located inside the operating room (Step 'O1') 801. The mentor surgeon starts the remote location workstation (Step 'M1') 901. During the start of both the workstation, connections with hardware units are checked, and corresponding status is displayed on the visualization screens. Both the workstations launch threads to continuously update: (i) the surgical state, (ii) tooltip poses, (iii) data to be communicated over network, and/or (iv) the rendered objects on visualization screen.

The mentor surgeon sends request to connect to operating room workstation (Step 'M2') 902. The request is then approved by the operating surgeon 802 and connection is established between operating room workstation and remote location workstation.

The operating surgeon then sets the instrument state (Step 'O2') 803 where the list of surgical instruments to be used in the surgery is added to the operating room workstation. The tracking frames are attached to the trocars (cannulas), registered with optical tracking system, and inserted inside patient. A tracking tool is used to select the incision points. For every trocar inserted inside the patient, a label is assigned to the incision point by the operating surgeon and the instrument state $S_{Instrument}(t)$ is updated on the operating room workstation. The instrument state $S_{Instrument}(t)$ is then shared by operating room workstation with the remote location workstation.

Similarly, the operating surgeon also sets the scope state (Step 'O3') 804 where a tracking frame is attached to the scope, registered with optical tracking system, and inserted inside patient. The operating surgeon sets the scope state 804 comprising of scope's field of view (FOV), scope's angulation, and rigid transformation between $M_{Scope(t)}$ and $M_{ScopeCamera}(t)$. The scope state is then also shared by operating room workstation with the remote location workstation. In some surgical procedures, the operating surgeon may set the scope state (Step 'O3') and then the instrument state (Step 'O2').

Once the instrument and scope states have been set, the operating surgeon observes the operating field on the visualization screen 805 and starts performing the surgery 806. The mentor also observes the surgery 903 as it is performed by the operating surgeon on the visualization screen of the remote location workstation. During the surgery if mentoring is required 807, the operating surgeon requests for mentoring 808. When the mentoring request is received by the mentor 904, the mentor checks if mapping is required 906; and if required, Step 'M3' 907 is performed mapping (i) surgical instrument type to an incision point label and (ii) left or right human computer interface (HCI) interface to an incision point label, thus updating the instrument state. The mentor interacts with the human computer interface 908 which in turn updates the tooltip poses of the rendered augmented tools on both the workstations. This provides mentoring in form of visual cues to the operating surgeon. An audio channel can also be used to communicate or raise mentoring request over the network.

When the surgery is completed 811, 905, both the operating room and remote location workstations are stopped 809, 909, and connection is released.

Figure 10:
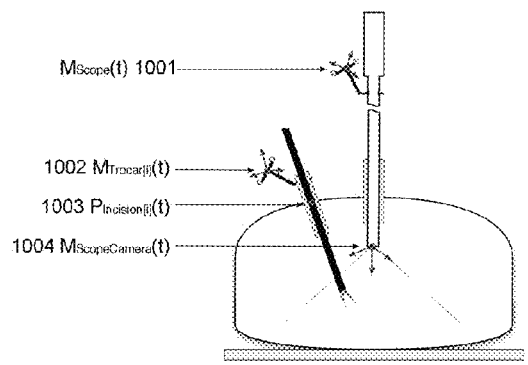
FIG. 10 shows the parameters describing the state of the system at time "t" according to some aspects of the present disclosure.
Figure 10:
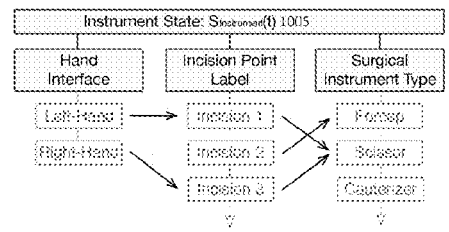
Figure 11:
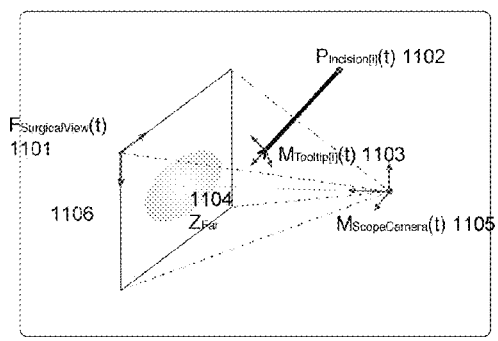
FIGS. 11 and 12 illustrate the rendering of visual information according to some aspects of the present disclosure.

FIG. 10 shows the parameters 1001-1005 describing the state of the system at time instance "t." FIGS. 11 and 12 illustrate the rendering of visual information according to some aspects of the present disclosure. The 'update display thread' continuously renders objects inside registration and augmentation window at both the workstations.

The Registration Window 1100 (FIG. 11) renders poses of tracking frames, pose of scope camera, location of the incision points (along with labels), the frustum of the surgical view (along with the updated surgical view frame), and pose of the augmented tools selected. The Augmentation Window 1200 (FIG. 12) displays the surgical view $F_{SurgicalView}(t)$ 1201 in the complete window and also displays augmented tools if selected by the mentor.

$M_{Scope}(t)$ 1001 represents the pose of the tracking frame attached to the scope in form of 4×4 homogenous transformation matrix for time instant "t." Similarly $M_{Trocar}[i](t)$ 1002 represents the pose of the tracking frame attached to i-th trocar in form of 4×4 homogenous transformation matrix for time instant "t." The poses are measured with respect to the coordinate system of the optical tracking system inside the operating room. Each tracking frame comprises of unique configuration of optical markers which corresponds to either the scope or one of the trocars.

The pose of scope camera is represented by 4×4 homogenous transformation matrix $M_{ScopeCamera}(t)$ 1004 at time instant "t." The "Z" axis coincides with the viewing direction of the scope camera and the 'X' and 'Y' axes are parallel to the sides of the rectangular surgical video frame captured by the scope camera. The scope tracking frame is attached onto the scope at a specific position and $M_{ScopeCamera}(t)$ 1004 is computed based upon the predefined rigid body transformation matrix between $M_{ScopeCamera}(t)$ 1004 and $M_{Scope}(t)$ 1001.

The x, y, and z ordinates of the incision point at time instant "t" is represented by $P_{Incision[i]}(t)$ 1003. Based on the pose $M_{Trocar[i]}(t)$ 1002, the corresponding $P_{Incision[i]}(t)$ 1003 is computed in two ways: (i) the trocar tracking frame is attached at a specific position on the trocar and $P_{Incision[i]}(t)$ 1003 is computed based upon the predefined rigid body translation of $M_{Trocar[i]}(t)$ 1002 origin; and (ii) $P_{Incision[i]}(t)$ 1003 can also be computed by storing $M_{Trocar[i]}(t)$ 1002 over a time interval and finding a point in the space around which the trocar tracking frame rotates in the given time interval.

A frame of the surgical video acquired by scope camera at time instant "t" is represented by $F_{SurgicalView}(t)$ 1101, 1201. A compression filter 1106 can be applied to the video frame acquired by scope camera at the operating room workstation and de-compressed at remote location. Surgical state $S_{Surgical}(t)$ at time instant 't' is defined by a tuple <$F_{SurgicalView}(t)$, $M_{ScopeCamera}(t)$, $P_{Incisions}(t)$>, which comprises of surgical view, pose of the scope camera, and ordinates of the incisions points. The $S_{Surgical}(t)$ is continuously updated by update surgical state thread running on both workstations.

The scope state $S_{Scope}(t)$ stores scope's FOV, scope's angulation, and transformation between $M_{Scope}(t)$ 1001 and $M_{ScopeCamera}(t)$ 1004. The instrument state $S_{Instrument}(t)$ 1005 stores: (i) surgical instrument types entered by the operating surgeon via the operating room workstation, (ii) incision point labels entered by the operating surgeon on the operating room workstation, (iii) transformation to obtain $P_{Incision[i]}(t)$ from $M_{Trocar[i]}(t)$ and (iv) mapping between (a) surgical instrument type to an incision point label and (b) left or right HCI interface to an incision point label entered by the mentor.

$M_{Tooltip[i]}(t)$ 1103 represents a co-ordinate frame in form of 4×4 homogenous transformation matrix attached to the tooltip of the augmented surgical instrument. The transformation of $M_{Tooltip[i]}(t)$ causes the augmented surgical instrument to move in the registration and augmentation window. $M_{Tooltip[i]}(t)$ is computed from the pose of the user interface defined by $M_{Interface[i]}(t)$.

The view rendered in the registration window 1100 can be rotated, zoomed, panned to get better understanding from different viewpoints. Scope's FOV is used to compute the frustum aspect ratio and the ZFar 1104 of the frustum can be adjusted such that $M_{Tooltip[i]}(t)$ 1103 is visible. As the surgical state $S_{Surgical}(t)$, instrument state $S_{Instrument}(t)$ 1005, tooltip poses $M_{Tooltips}(t)$ 1202 is set or updated, the registration window starts displaying the corresponding changes. The pose of the augmented tool (to be rendered for mentoring) is computed by the kinematics models loaded for the selected surgical instrument type. During computations, the pose of the last joint (end-effector) of the kinematics chain is defined by $M_{Tooltip[i]}(t)$ 1103 with respect to a base frame defined at incision point.

The view of the augmentation window 1200 is fixed (i.e. cannot be rotated, zoomed, panned). The augmented tool is rendered as if the window is viewed from the pose of $M_{ScopeCamera}(t)$. The augmented tool is displayed only when requested by the operating surgeon to enable mentoring.

The registration window is used to track the relative poses during setting the instrument and the scope state. It also assists mentor to understand the surgical setup inside operating room. The augmentation window is used to provide mentoring to the operating surgeon via visual cues in form of the augmented surgical instruments.

Figure 13B:
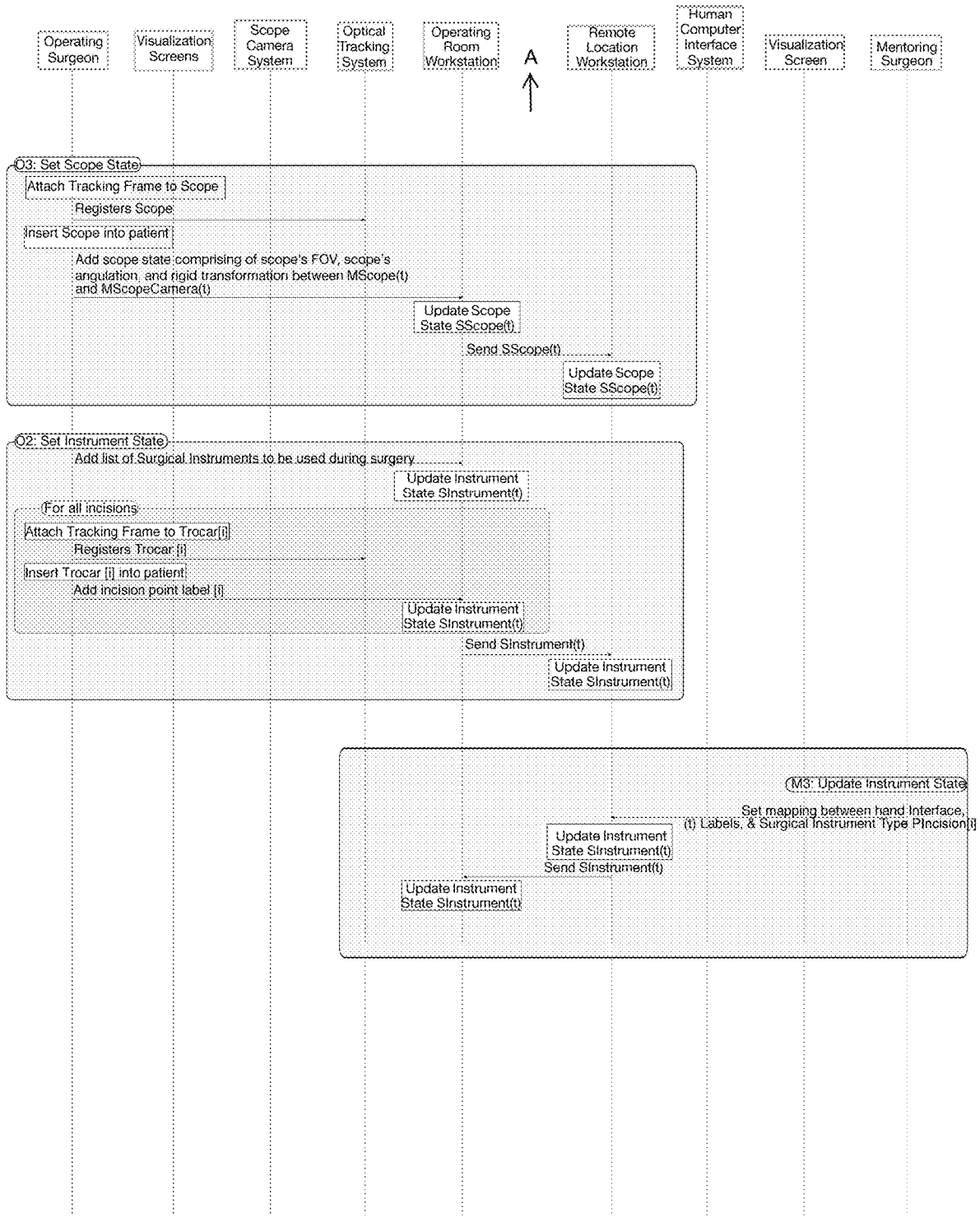
Figure 14A:
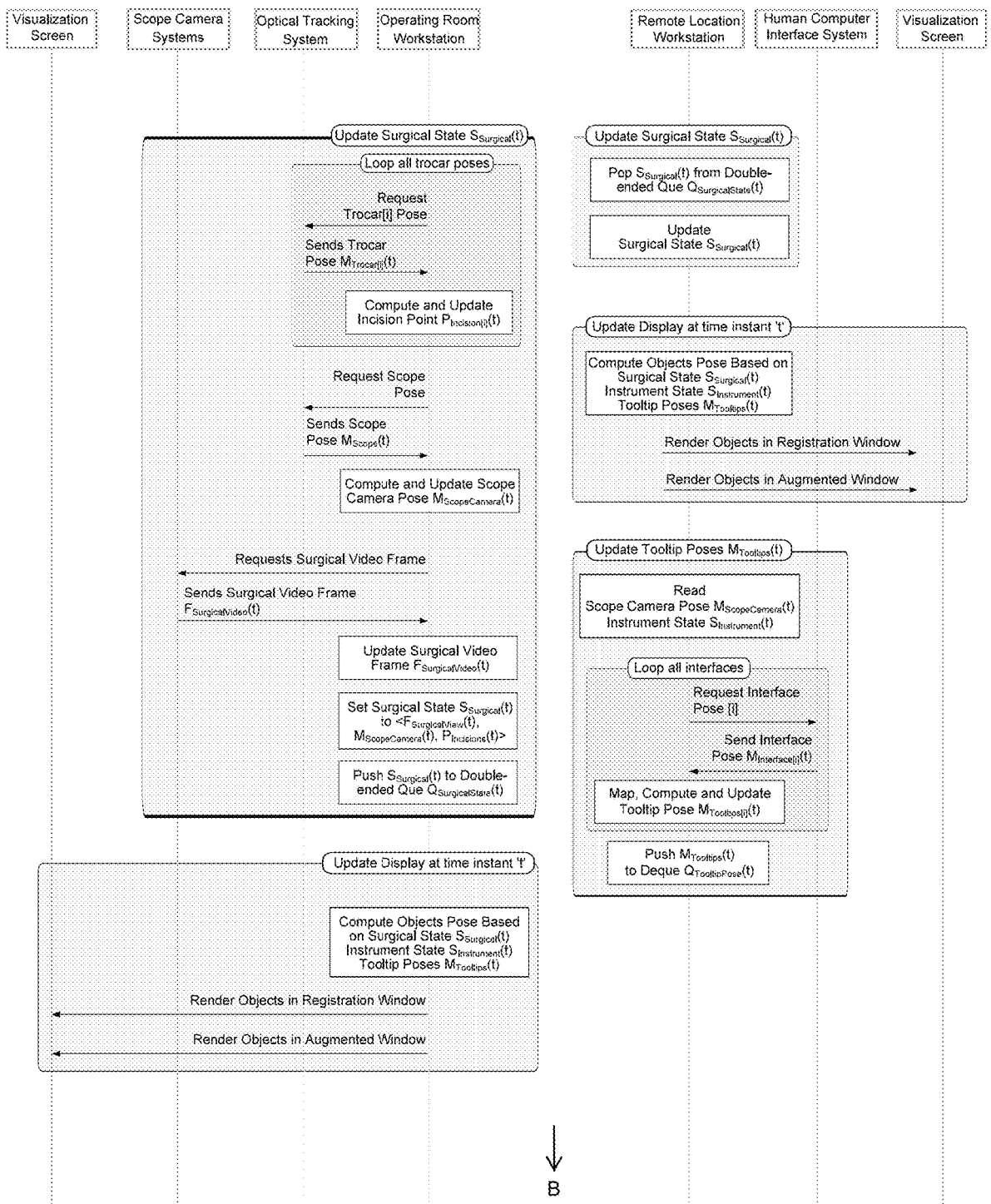
FIGS. 14A and 14B illustrate the sequence of operations performed by the launch threads according to some aspects of the present disclosure.
Figure 14B:
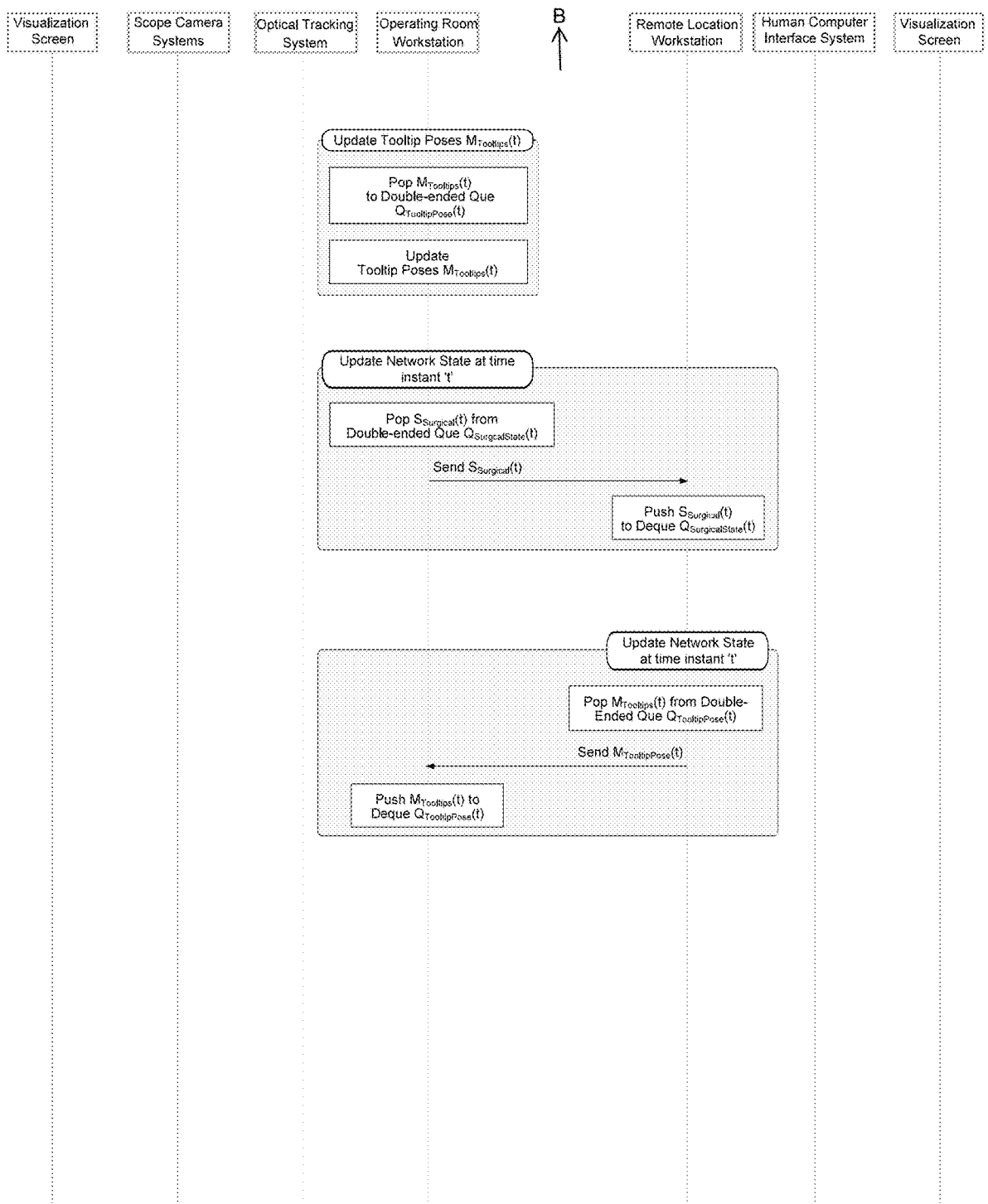

FIGS. 13A-15 illustrate the interaction among the hardware components shown in FIGS. 6A-7B. FIGS. 13A and 13B illustrate the sequence of steps performed by the operating surgeon and the mentor in some embodiments. Specifically, FIGS. 13A and 13B illustrate communication among these hardware components when the steps (O1, O2, O3, M1, M2, M3) presented in FIGS. 8-9 workflows are executed. Steps O1 and M1 launch threads (parallel running tasks) which are shown in FIGS. 14A and 14B. FIGS. 14A and 14B illustrate the sequence of operations performed by the launch threads in some embodiments. Each of these threads can be considered as software modules running on the operating room workstation and remote location workstation.

Figure 15A:
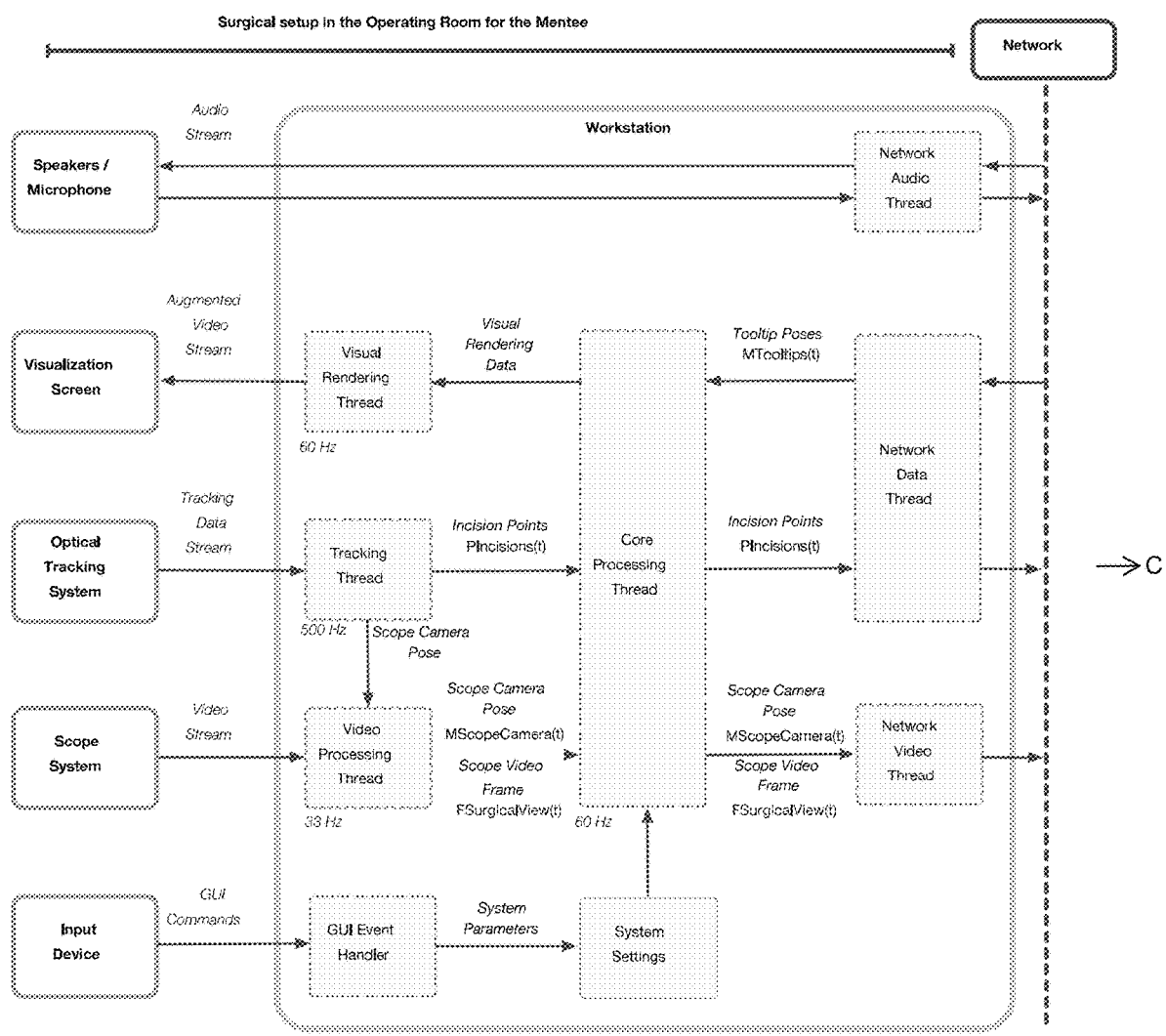
FIGS. 15A and 15B illustrate interactions between the hardware and software components of the operating room setup and the remote location setup according to some aspects of the present disclosure.
Figure 15B:
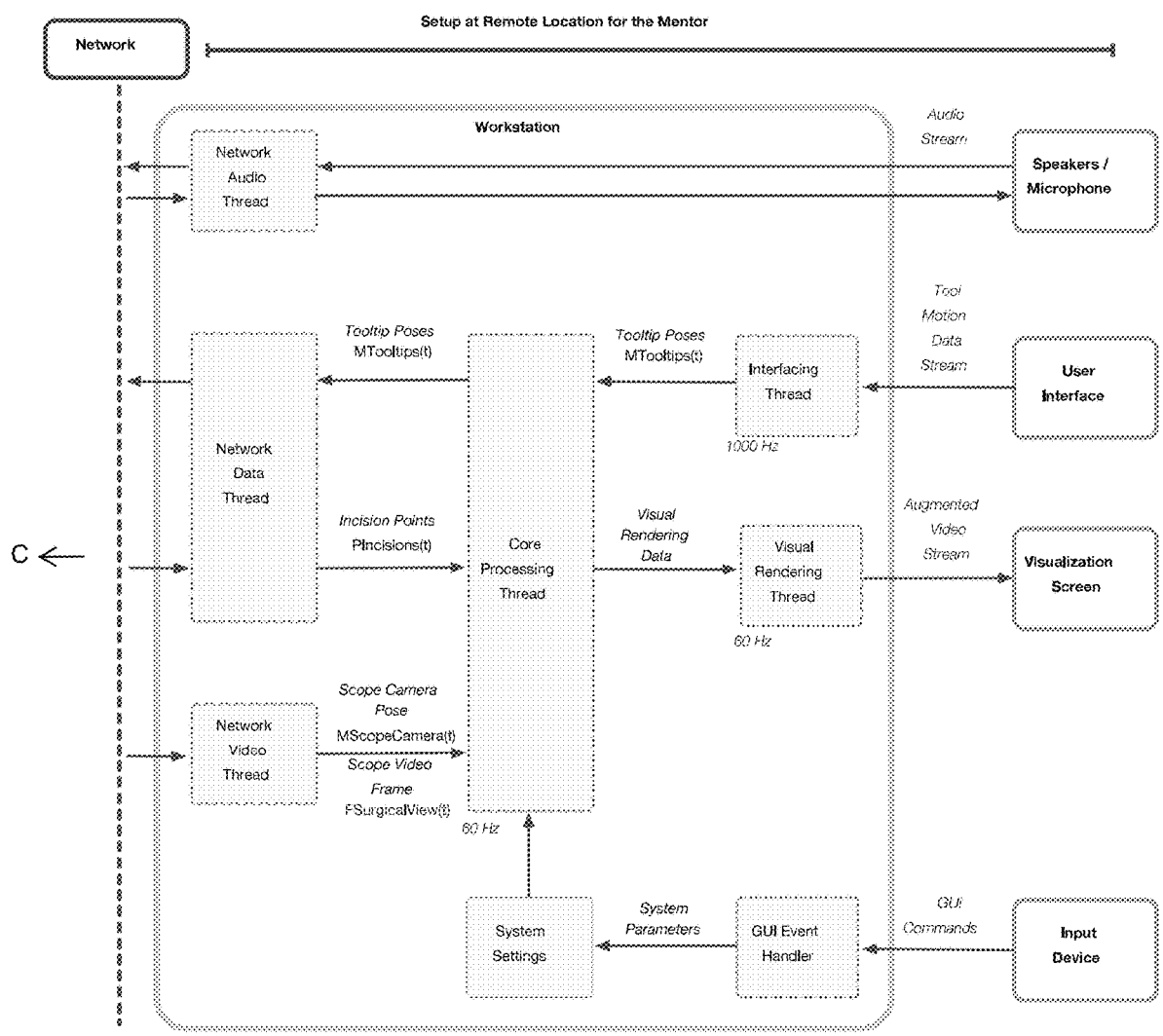

FIGS. 15A and 15B illustrate a further embodiment of the architecture of tele-mentoring. In this example, the Web Real Time Communication (WebRTC) framework was used in lieu of the Real-Time Messaging Protocol (RTMP) server. Use of the WebRTC framework enabled tele-mentoring across geographical boundaries, reducing the latency in sending data over the network, and enabled audio communications. Use of WebRTC enabled real-time communication capabilities including video, audio, and data to be exchanged between workstations. The networking threads were native to WebRTC.

To establish a connection, the operating room workstation and the remote location workstation utilized a public IP using a Session Traversal Utilities for Network Address Translators (NAT) (STAN) server. A signaling server was used to exchange the public IPs along with the media formats used by the networking threads. A direct peer-to-peer connection was established between the two workstations to initiate the communication required for tele-mentoring, as seen in FIGS. 15A and 15B.

Figure 16:
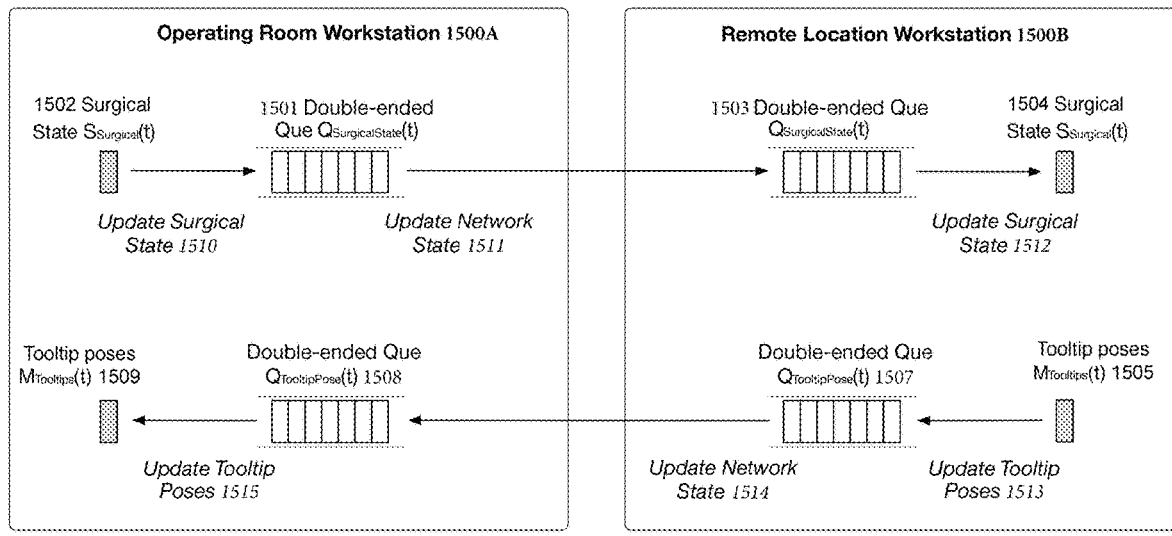
FIG. 16 is an example schematic of data packets transferred over network according to some aspects of the present disclosure.

FIG. 16 is an example schematic of data packets transferred over network according to some aspects of the present disclosure. Double-ended queues 1501, 1503, 1507, 1508 are used at both operating room workstation 1500A and remote location workstation 1500B to buffer and transfer surgical states $S_{Surgical}(t)$ 1502,1504 and Tooltip poses $M_{Tooltips}(t)$ 1505, 1509. At operating room workstation 1500A, the 'update surgical state' 1510 thread pushes the $S_{Surgical}(t)$ 1502 into double-ended que $Q_{SurgicalState}(t)$ 1501, whereas 'update network state' 1611 thread pops the $S_{Surgical}(t)$ 1502 from $Q_{SurgicalState}(t)$ 1501 on the operating room workstation 1500A and pushes it onto the $Q_{SurgicalState}(t)$ 1503 on the remote location workstation 1500B. The 'update surgical state' 1512 thread on the remote location workstation 1500B pops SSurgical(t) and updates the $S_{Surgical}(t)$ 1504 at remote location. Similarly, 'update tooltip poses' 1513 and 'update network state' 1514 threads at remote location workstation 1500B and 'update tooltip poses' 1515 thread at operating room workstation 1500A are used to transfer and update tooltip poses from the remote location to the operating room.

Figure 17:
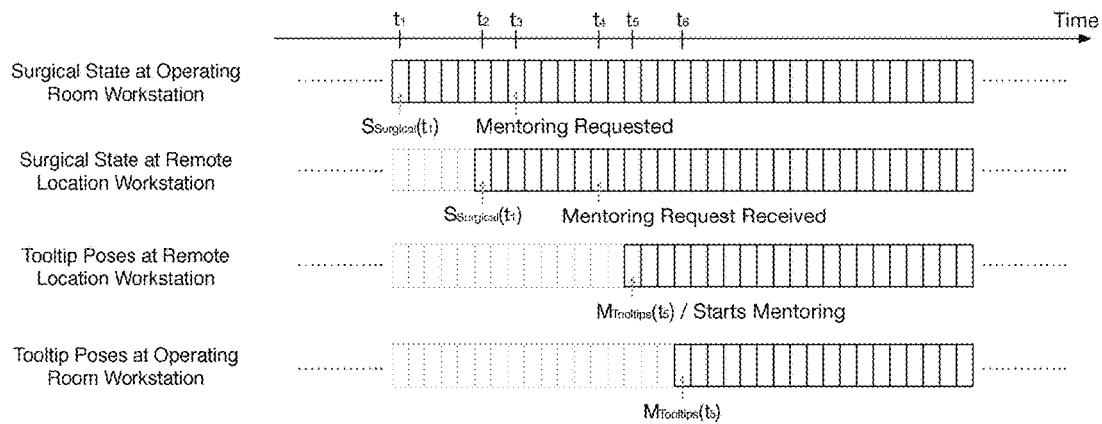
FIG. 17 illustrates the buffering of surgical states in case of for slow network connections according to some aspects of the present disclosure.

FIG. 17 illustrates the buffering of surgical states in case of for slow network connections according to some aspects of the present disclosure. In the figure, $t_1$ is when the operating room workstation starts sending surgical state to remote location; $t_2$ is when the remote location workstation receives surgical state from operating room workstation; $t_3$ is when the operating surgeon requests for mentoring; $t_4$ is when mentoring request is received by mentoring surgeon; $t_5$ is when the mentor interacts with HCI and remote location workstation starts sending tooltip poses to operating room; and $t_6$ is when the operating room workstation receives tooltip poses from remote location.

The operating room workstation will sequentially buffer surgical states $S_{Surgical}(t)$ from time instant '$t_5-(t_4-t_3)$' till '$t_5+(t_6-t_5)$', i.e. for time interval '$(t_6-t_5)+(t_4-t_3)$', where $(t_4-t_3)=(t_2-t_1)$ is network delay in sending/receiving $S_{Surgical}(t)$ from operating room to remote location workstation and $(t_6-t_5)$ is network delay in sending/receiving $M_{Tooltips}(t)$ from remote location to operating room workstation.

At $t_6$, if the components of surgical states $S_{Surgical}(t_6)$ and $S_{Surgical}(t_3+t_5-t_4)$ differ significantly, the operating room workstation may map $M_{Tooltips}(t_5)$ with $S_{Surgical}(t_3+t_5-t_4)$ for rendering of objects in augmented window. This featured, if required, can be activated in case of significant network delays.

Example User Interface Designs

Figure 18:
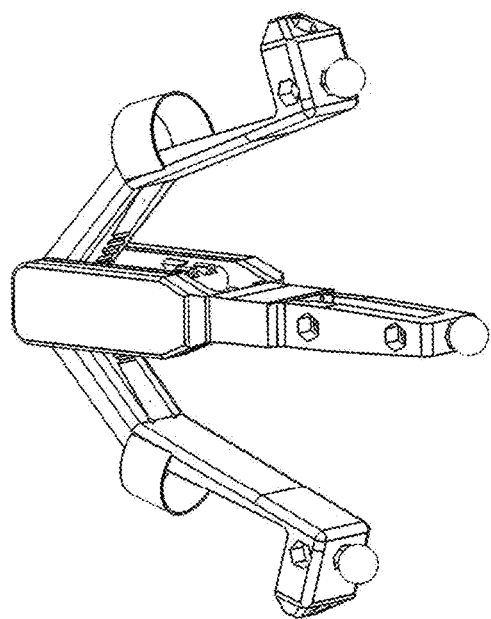
FIGS. 18-19 show an example user interface design according to some aspects of the present disclosure.
Figure 19:
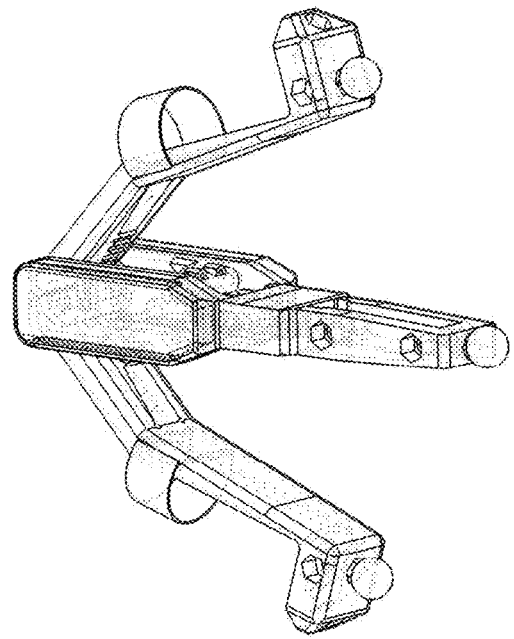
Figure 20:
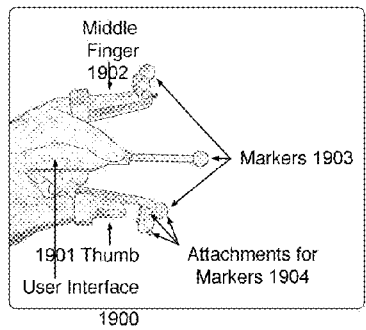
FIGS. 20-22 illustrate how a user's hand controls the user interface according to some aspects of the present disclosure.
Figure 21:
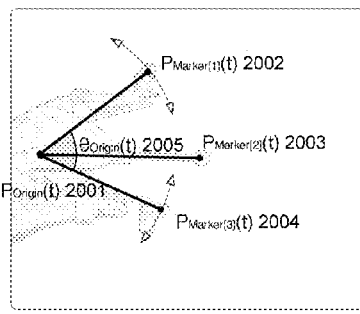
Figure 22:
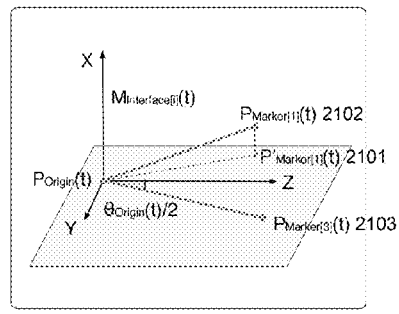
Figure 23:
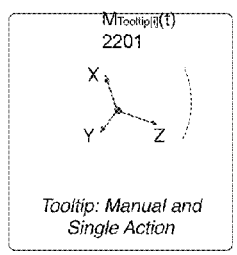
FIG. 23 illustrates an example manual and single action of the tooltip according to some aspects of the present disclosure.
Figure 24:
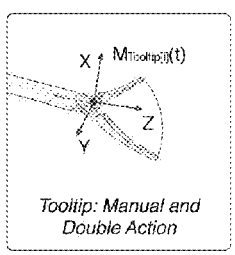
FIG. 24 illustrates an example manual and double action of the tooltip according to some aspects of the present disclosure.
Figure 25:
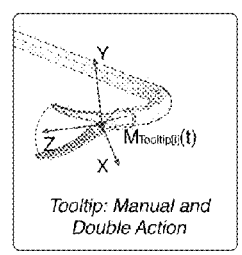
FIG. 25 illustrates an example manual and double action of the tooltip according to some aspects of the present disclosure.
Figure 26:
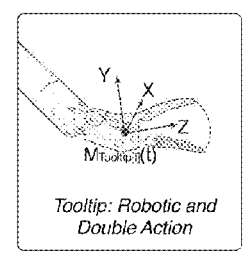
FIG. 26 illustrates an example robotic and double action of the tooltip according to some aspects of the present disclosure.

FIGS. 18-19 show an example user interface design. As illustrated in FIGS. 20-22, the mentoring surgeon holds the user interfaces 1900 in each hand. The user interface 1900 is part of the human machine interface system. The user interface 1900 is equipped with (a) pinching mechanism to constrain the motion of the mentor's middle/index finger 1902 and thumb 1901 with respect to each other and (b) mechanism to attach markers 1903, 1904 (at different positions near the distal end) to trace the motion as well as opening/closing of the user interface in the presence of sensors.

The markers can be passive (composes of retro-reflective material) or active (comprising of infrared LEDs) in nature, in form of spheres of different diameters or linear strips with different curvature, and tracked by human machine interface system's one or more optical tracking cameras/sensors placed in configuration to minimize occlusion. The position $P_{Marker[i]}(t)$ of the markers (i=1 to 3) is triangulated by these cameras/sensors.

The pinching of the user interface causes the markers to rotate around a revolute joint situated at $P_{Origin}(t)$ 2001. The point $P_{Origin}(t)$ 2001 is computed by solving equations taking in considerations the distance between the three markers $P_{Marker[i]}(t)$ 2002-2004 and the revolute joint $P_{Origin}(t)$ 2001 is constant, i.e. $\|P_{Marker[I]}(t), P_{Origin}(t)\|=Li$ where i=1 to 3 and Li depends upon the design of user interface and the location where markers are attached at distal end of the user interface. A plane passing through the point $P_{Origin}(t)$ 2001 and orthogonal to the axis of rotation for the markers is defined. Any marker $P_{Marker[i]}(t)$ 2002-2004 which does not lie on the plane, its projection $P'_{Marker[i]}(t)$ 2101 is computed on the plane. The angle $\theta_{Origin}(t)$ is computed as the angle substituted by line segments joining the two points $P_{Marker[1]}(t)$ 2102 and $P_{Marker[3]}(t)$ 2103 (or their projections $P'_{Marker[1]}(t)$ and $P_{Marker[3]}(t)$ at $P_{Origin}(t)$. The pose of the user interface is defined by $M_{Interface[i]}(t)$. $M_{Interface[i]}(t)$ represents a co-ordinate system frame with origin as $P_{Origin}(t)$, X-axis passing through $P_{Origin}(t)$ and orthogonal to the plane, Z-Axis passing through $P_{Origin}(t)$ and lies on the plane such that it bisects the angle $\theta_{Origin}(t)$, and Y-axis orthogonal to both Z and X axes.

FIGS. 23-26 illustrate the actions of the augmented surgical instrument tooltip in some embodiments. $M_{Tooltip[i]}(t)$ 2201 represents a co-ordinate frame attached to the tooltip of the augmented surgical instrument. The origin of $M_{Tooltip[i]}(t)$ coincides with the revolute joint of the tooltip. The Z-Axis extends outwards as the distal end and X-Axis is orthogonal to plane of rotation of the tooltips.

The transformation of $M_{Tooltip[i]}(t)$ causes the augmented surgical instrument to move. The relative motion of $M_{Interface[i]}(t)$ is mapped to the relative motion of $M_{Tooltips[i]}(t)$ representing the tooltips of the augmented surgical instrument, i.e. $\Delta MTooltips[i](t)=f2(f1(\Delta M_{Interface[i]}(t)))$, where $\Delta M_{Tooltips[i]}(t)$ and $\Delta M_{Interface[i]}(t)$ shows the relative motion measured with respect to $M_{Tooltips[i]}(t_0)$ and $M_{Interface[i]}(t_0)$ at time instant $t_0$, respectively. $\Delta M_{Interface[i]}(t)$ is measured with respect to the human computer interface system reference frame. Function $f2$ transforms and scales the relative motion $\Delta M_{Interface[i]}(t)$ with respect to the scope camera reference frame $M_{ScopeCamera}(t)$. $f2$ removes any unwanted poses (which are not feasible based on the constrains impose either on the movement of the surgical instrument by the incision point or feasible kinematic model of the instrument itself) and maps $f1(\Delta M_{Interface[i]}(t))$ to the most appropriate pose to represent the augmented surgical instrument tooltips. The opening/closing of the user interface determines $\theta_{Origin}(t)$ 2005, which in turn determines the opening and closing of the augmented surgical instrument tooltips.

Figure 27:
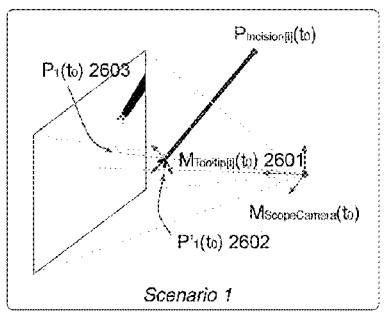
FIGS. 27-28 illustrate example scenarios of the pose $M_{Tooltip[i]}(t_0)$ of the augmented surgical instrument tooltip at time instant to according to some aspects of the present disclosure.
Figure 28:
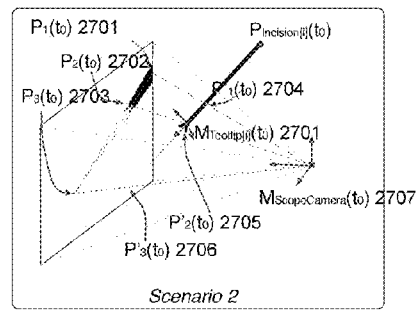

FIGS. 27-28 illustrate example scenarios of the pose $M_{Tooltip[i]}(t_0)$ 2601,2701 of the augmented surgical instrument tooltip at time instant $t_0$. In Scenario 1, the $M_{Tooltip[i]}(t0)$ is positioned at a point $P'_1(t_0)$ 2602 such that its projection $P1(t_0)$ 2603 is at a fixed aspect ratio from the center position of the video frame FSurgicalView($t_0$). In Scenario 2, computer vision techniques can be used to process video frame FSurgicalView($t_0$) to locate points $P1(t_0)$ 2701, $P_2(t_0)$ 2702, and $P_3(t_0)$ 2703 on the video frame and $P_1'(t_0)$ 2704, $P_2'(t_0)$ 2705, and $P_3'(t_0)$ 2706 within the frustum of $M_{ScopeCamera}(t_0)$ 2707 such that the position of $M_{Tooltip[i]}(t_0)$ 2701 overlaps onto the surgical instrument tooltip position observed in the video frame $F_{SurgicalVview}(t_0)$ and the shaft of the augmented surgical instrument overlaps onto surgical instrument shaft observed in the video frame $F_{SurgicalView}(t_0)$.

First Testing of Tele-Mentoring Framework

Referring to FIGS. 29A-30E, the tele-mentoring framework of the architecture depicted in FIGS. 7A and 7B was tested on a surgical phantom for a minimally invasive manual surgery as well as a robotic surgery. The testing included a hemispherical surgical phantom with five incision points, which simulated a pneumoperitoneum during surgery and a silica gel structure inside the phantom to mimic the surgical field when observed using a scope.

FIGS. 29A-29D shows an exemplary minimally invasive manual surgical setup. FIGS. 8A-8C illustrate the operating room setup, the surgical phantom used to mimic incisions and surgical field, and the remote location setup, respectively. FIG. 8D illustrates the view of the surgical setup schematically for the manual surgical setup.

Figure 29A:
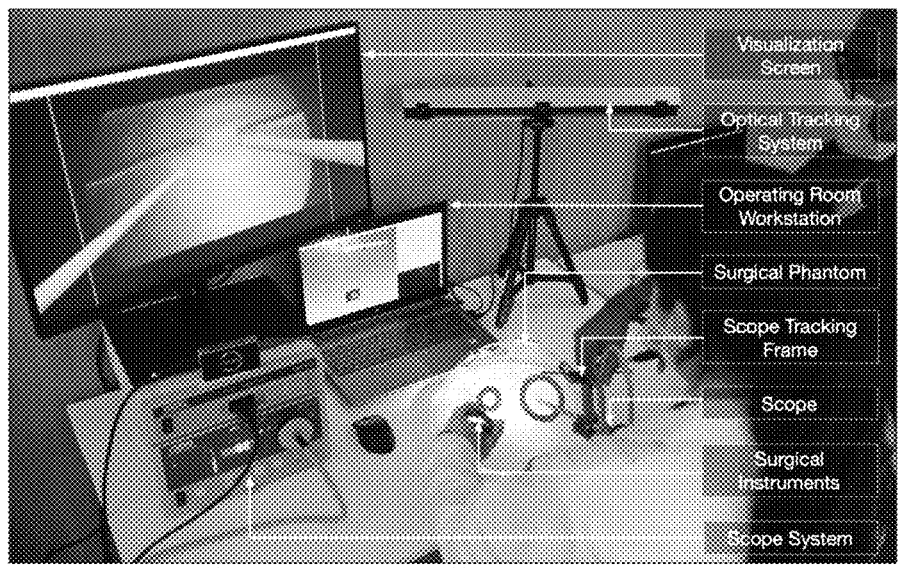
FIGS. 29A-29D shows an exemplary minimally invasive manual surgical setup, including (A) the operating room setup, (B) the surgical phantom used to mimic incisions and surgical field, (C) the remote location setup, and (D) illustrates the view of the surgical setup schematically for the manual surgical setup, respectively.
Figure 29B:
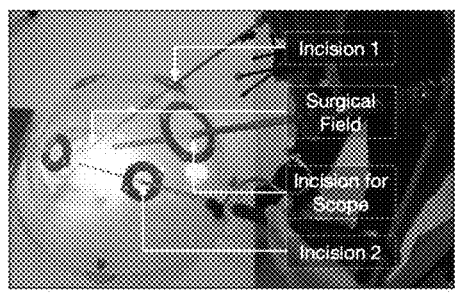
Figure 29C:
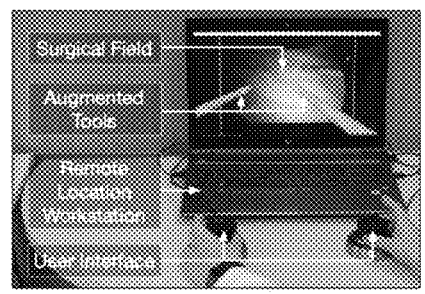

The manual surgical setup of FIGS. 29A-29D included a camera head by Karl Storz®, IMAGE1 S™, a light source by Karl Storz®, Model #201331 20, and a video processor by Karl Storz®, Model #222010 20. The surgical instruments included an angulated laparoscope (30-degree, 8 mm, Karl Storz®) and laparoscopic instruments (Richard Wolf® Laparoscopic Needle Holder) as shown in FIG. 29B. An adapter (Magewell® USB Capture HDMI 4K Plus) converted the SDI video output from the video processor to a USB-C port of the operating room workstation. At the remote location workstation, SpaceMouse® devices (3DConnexion) were used as the user interface to control virtual models of EndoWrist® instrument tooltips as shown in FIG. 29C.

FIGS. 30A-30E show an exemplary minimally invasive robotic surgical setup. FIGS. 9A-9D illustrate the operating room setup, the view from the master console, the surgical phantom used to mimic incisions and surgical field, and the remote location setup, respectively. FIG. 9E illustrates the view of the surgical setup schematically for the robotic surgical setup.

Figure 30A:
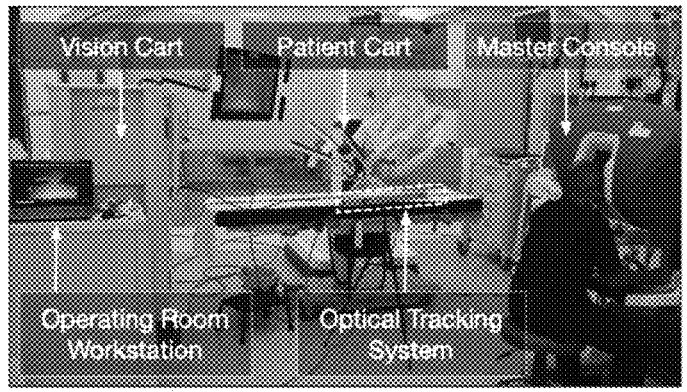
FIGS. 30A-30E show an exemplary minimally invasive robotic surgical setup, including (A) the operating room setup, (B) the view from the master console, (C) the surgical phantom used to mimic incisions and surgical field, (D) the remote location setup, and (E) the view of the surgical setup schematically for the robotic surgical setup, respectively.
Figure 30B:
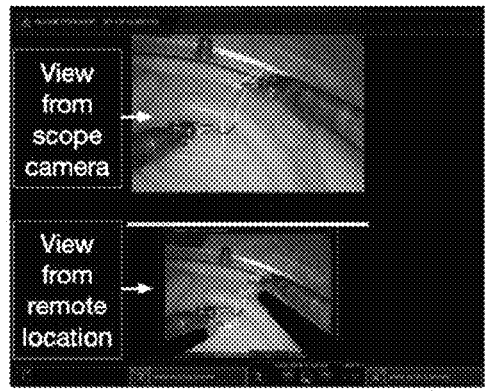
Figure 30C:
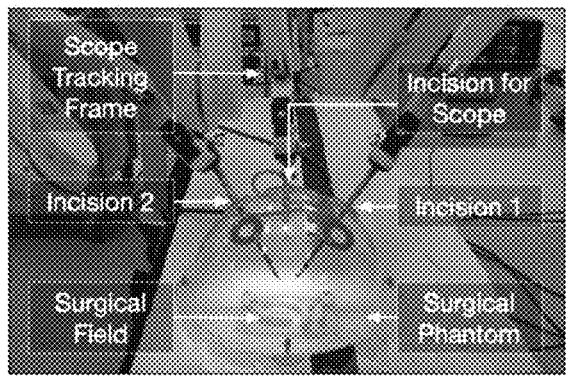
Figure 30D:
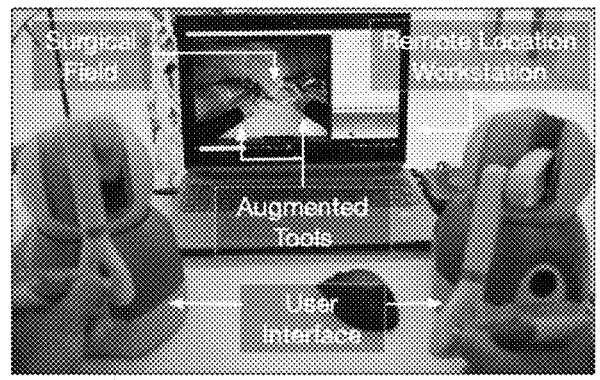

The robotic surgical setup of FIG. 30A was tested on Da Vinci Xi® surgical robot by Intuitive Surgical Inc. The output video stream from the vision cart was connected to the operating room workstation of the tele-mentoring framework using an adapter (Magewell® USB Capture HDMI 4K Plus). The augmented view from the operating room workstation of the tele-mentoring framework was rendered in tile-pro on the surgeon's console mode side-by-side with the view from the scope as shown in FIG. 30B. The surgical instruments include a 30-degree angulated scope and EndoWrist® instruments (470006, large needle drivers) as shown in FIG. 30C. At the remote location workstation of the tele-mentoring framework, Touch™ devices (3D Systems) were used as user-interface to control virtual models of EndoWrist® instruments as seen in FIG. 30D.

Figure 29D:
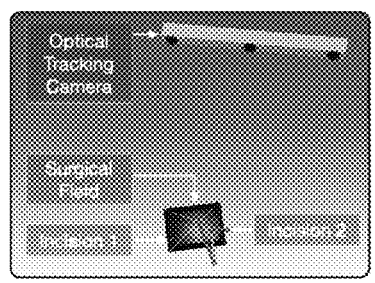
Figure 30E:
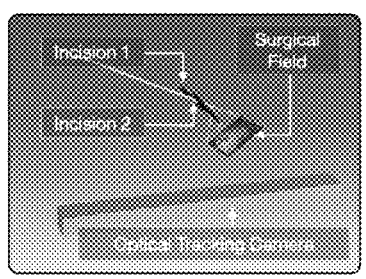

FIG. 29D and FIG. 30E illustrate the manual and robotic surgery views, respectively, of the surgical setup, depicted schematically in FIG. 11. Similarly, FIG. 29A and FIG. 30B illustrate the manual and robotic augmented views, respectively, of the surgical setup, depicted schematically in FIG. 12. The motion of the virtual tools performed by the operator at the remote location workstation was observed by the operator inside the operating room workstation on the augmented view.

Results of First Testing of Tele-Mentoring Framework

The manual and robotic systems were tested multiple times over varying time periods of 8 minutes, 10 minutes, and 12 minutes, with three trials per time period. The clocks on the remote and operating room workstations were synchronized from a common server, Windows Time service (W32Time). The data sent and received over the network at both ends was logged and processed to evaluate the functioning of the tele-framework over the network.

The surgical state $S_{SurgicalState}(t)$, comprising of incision points $P_{Incisions}(t)$, scope pose $M_{ScopeCamera}(t)$, and surgical view $F_{SurgicalView}(t)$, was sent over the network from the operating room to the remote location workstation. The position of the incision points $P_{Incisions}(t)$ was marked using a tracking tool. The position remained stationary during the study, as the surgical phantom was not moved. The pose of the scope's camera $M_{ScopeCamera}(t)$ was continuously sent over the network from the operating room to the remote location.

Figure 31B:
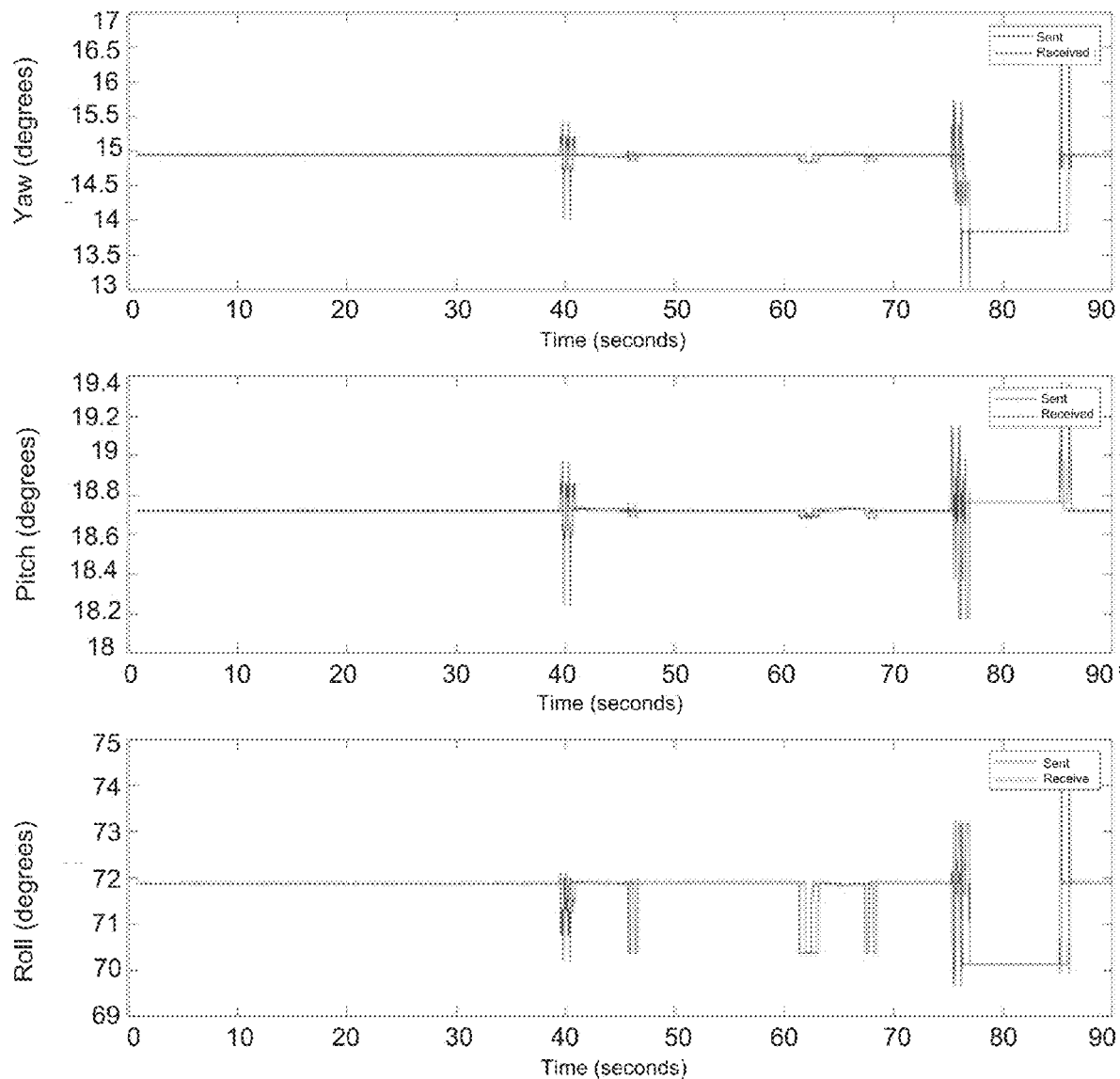
FIGS. 31A-34B illustrate data related to a first testing of tele-mentoring workstations as shown in FIGS. 29A-29E and FIGS. 30A-30E.

FIGS. 31A and 31B illustrate the graphical representation of the delay in receiving information at a remote location from the operating room. The pose of the scope camera $M_{ScopeCamera}(t)$ is acquired at the operating room and sent to the remote local workstation, and FIGS. 31A and 31B present $M_{ScopeCamera}(t)$ decomposed into position (translations along X, Y, and Z axes) and orientation (rotations along X, Y, and Z axes) measured with respect to optical tracking system. The remote local workstation received $M_{ScopeCamera}(t)$ with a delay. The poses are expressed as translation (in X, Y, and Z axes) and rotations (roll, yaw, and pitch) with respect to the time and are measured in the optical tracking system coordinate system.

An average delay of 1.560±0.426 seconds was observed while transferring $S_{SurgicalState}(t)$ from the operating room to the remote location workstation. The delay was computed by taking difference of the logged timestamps for the received and sent $S_{SurgicalState}(t)$ at the remote and operating room workstations, respectively.

Figure 32A:
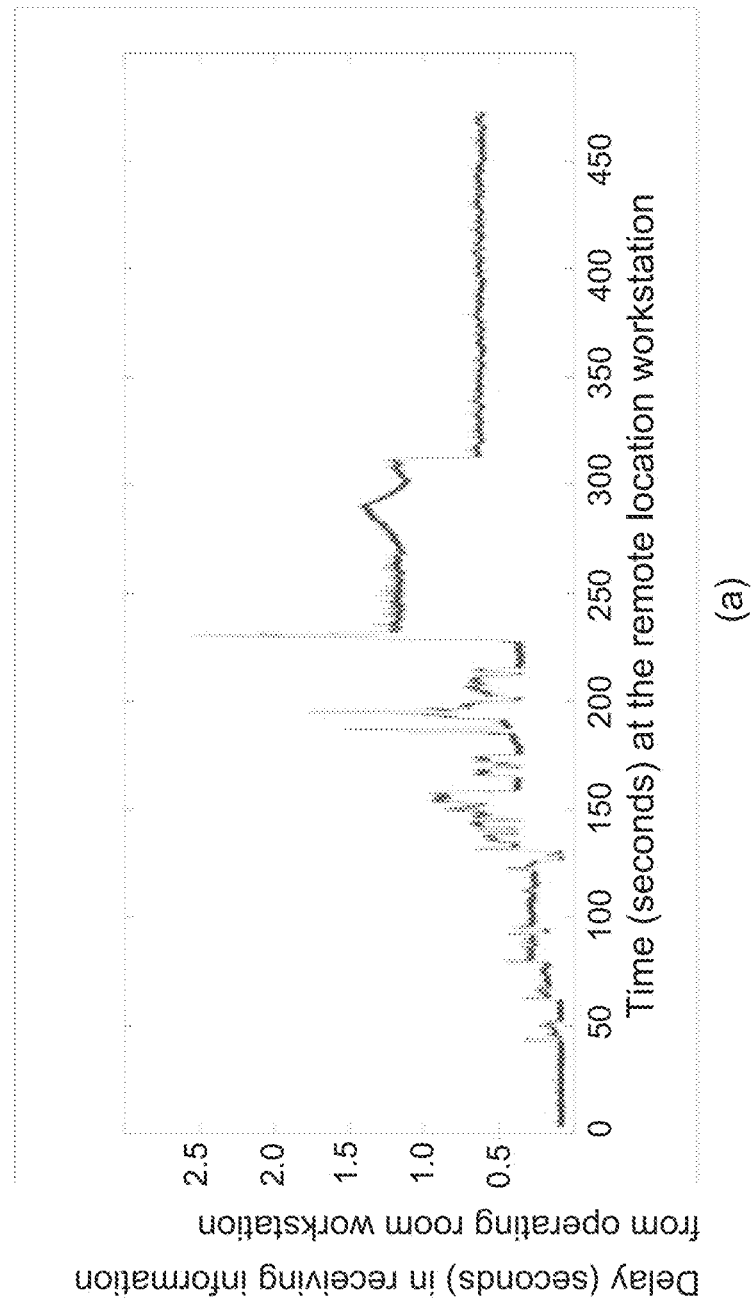

FIG. 32A illustrates the variation in delays between the same surgical state $S_{SurgicalState}(t)$ sent and received for one such trial. To correlate $F_{SurgicalView}(t)$ at sender and receiver ends, a timestamp was written on the image of the surgical view frame $F_{SurgicalView}(t)$ at the sender's end and extracted at receiver's end. No drop of $S_{SurgicalState}(t)$ packets was observed.

Figure 32B:
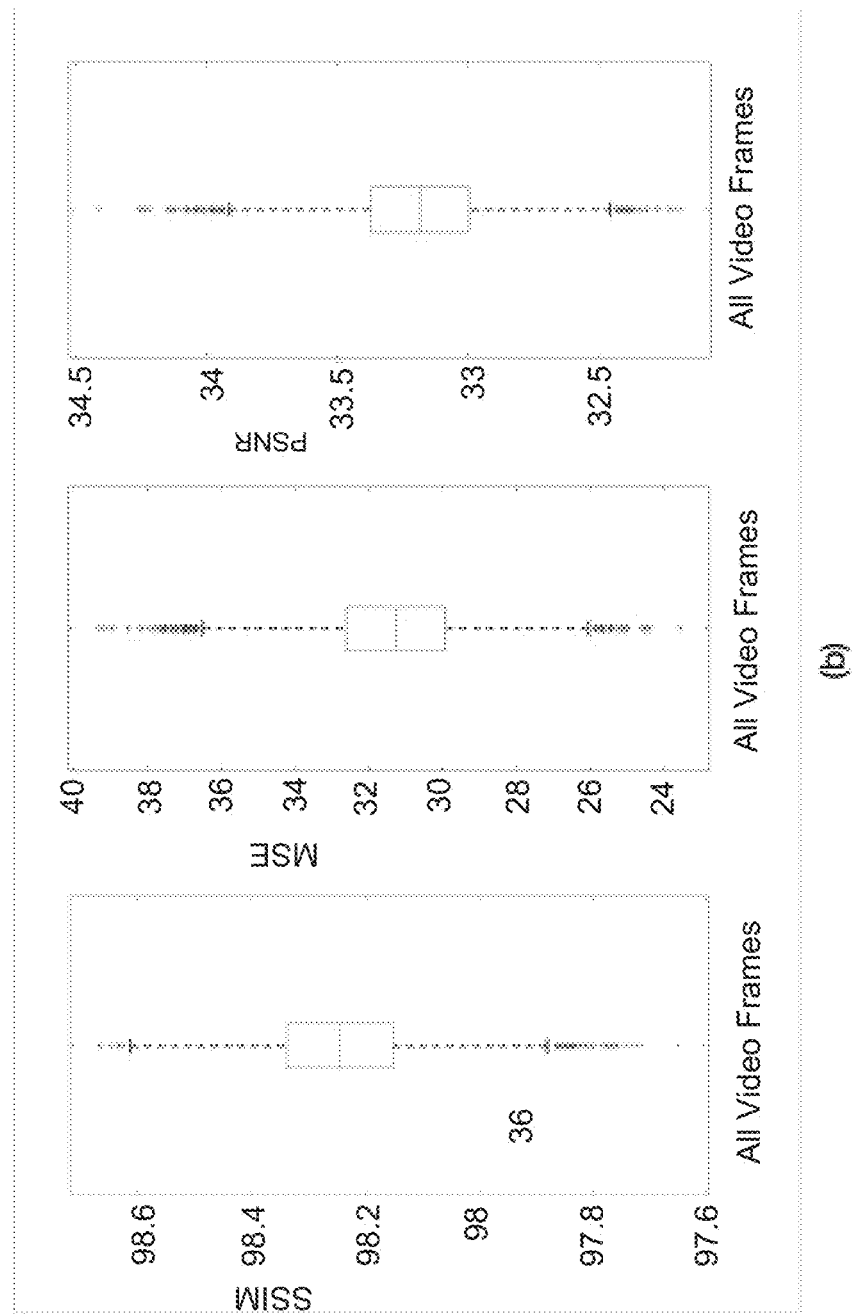

Before sending the $F_{SurgicalView}(t)$ over the network, the video stream is encoded by the network module in the operating room workstation and then decoded by the network module of the remote location workstation. The video image quality metrics were used to compare the quality of sent frames before encoding and received frames after decoding. The computed values of the video image quality metrics were: the average mean square error (MSE) of 31.28, the average peak signal-to-noise ratio (PSNR) of 33.18, and the average structural similarity index measure (SSIM) of 98.24% as shown in FIG. 32B.

Figure 33:
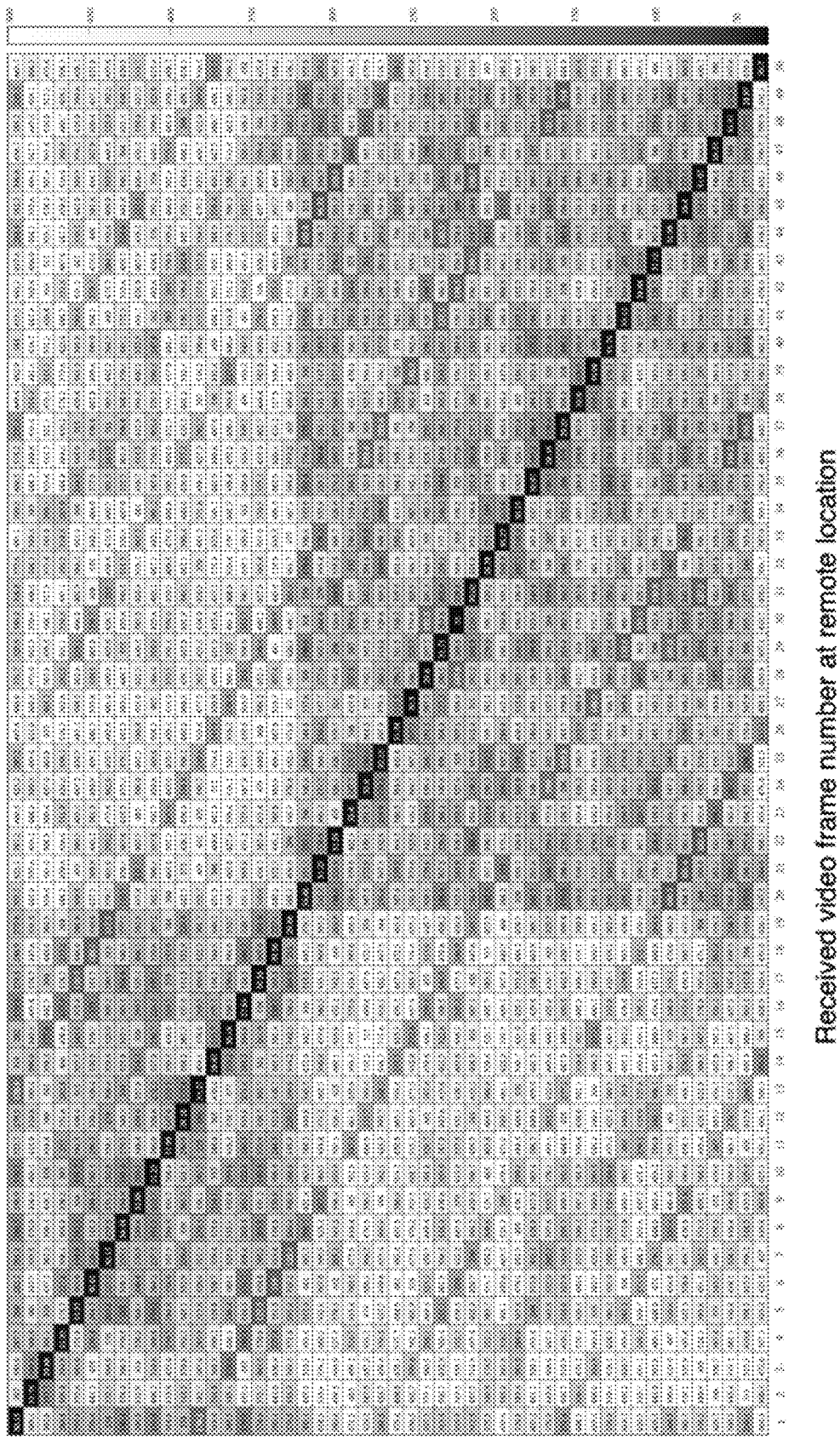

FIG. 33 shows a heat map of the MSE values for a sample of 50 video frames sent from the operating room as compared with the 50 video frames received at the remote location. The heat map was generated to understand the relative value of MSE for video frames with respect to each other. The value is minimum for the same video frame number sent and received, and is seen along the diagonal of the heat map.

Figure 34A:
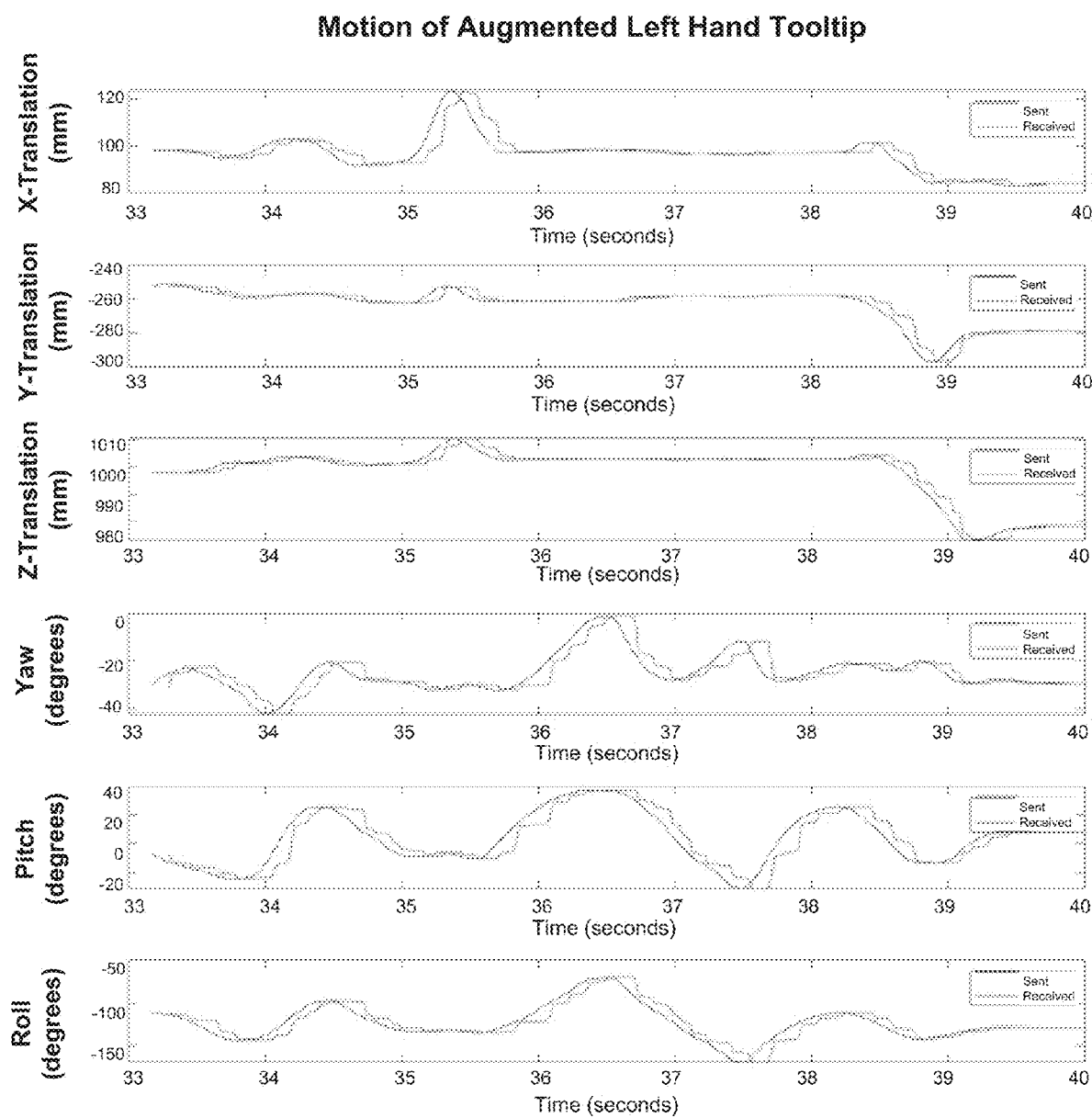
Figure 34B:
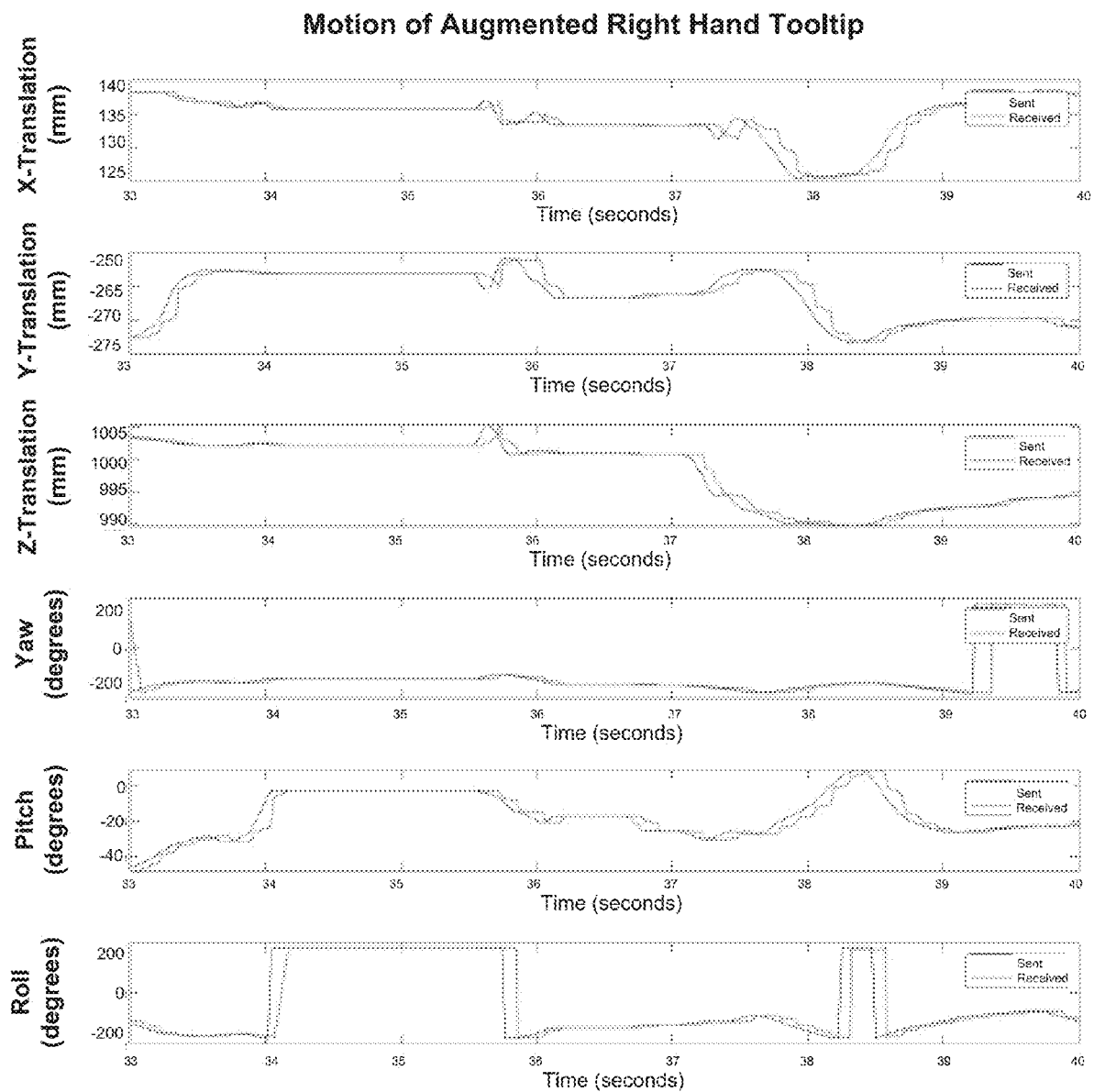

When the virtual instruments were selected by the operator at the remote location workstation, tooltip poses $M_{Tooltips}(t)$ were sent over the network from the operating room to the remote location workstation. FIGS. 34A and 34B show $M_{Tooltips}(t)$ for the movements of the left and right augmented tools. An average delay of 0.089±0.017 seconds was observed while transferring $M_{Tooltips}(t)$ from the remote location to the operating room workstation. The delay was computed by taking difference of the logged timestamps for the received and send $M_{Tooltips}(t)$ at the operating room and remote workstations, respectively. It was observed that the packets sent from the remote location workstation were received in batches at the operating room workstation as shown in FIGS. 34A and 34B. A buffer was therefore required to consume the packets at a uniform rate. When there is an update in the instrument state $S_{Instrument}(t)$, it is sent asynchronously over the network between the operating room to the remote location workstation.

Discussion of the Results of First Testing of Tele-Mentoring Framework

The information pertaining to the surgical field is transferred over the network from the operating room to the remote location with an average delay of 1.560±0.426 seconds. At the remote location, the mentor surgeon performs the motion of augmented tools, which is sent to the operating room at an average delay of 0.089±0.017 seconds, which is within the limit of 0.20 seconds. This delay is acceptable, when the surgical field to be operated is stable. The recommendation provided by the Society of American Gastrointestinal and Endoscopic Surgeons (SAGES) requires a latency of less than 0.45 seconds for live tele-mentoring.

Low latency is important, particularly during live surgery, to ensure the remote surgeon is aware of the operating field and can mentor as complications evolve intraoperatively. Also, the tissue motion caused by breathing or heartbeat would require the $F_{SurgicalView}(t)$ received at the remote location to be synchronized with $M_{Tooltips}(t)$ and sent back to the operating room to be visualized on a separate visualization screen.

The setups of FIGS. 29A-29D and 30A-30E were tested on a local area network, instead of the Internet. Use of an Internet connection would require the RTMP server to be hosted on a cloud hosting service and access to network ports by the service providers, which may affect the delays in transferring the information. An alternative method is to use low latency live streaming protocols, such as WebRTC™, to overcome the delays and dependencies on service providers. This could be achieved by changing the networking modules without affecting the remaining modules of the system.

Further, in the setups of FIGS. 29A-29D and 30A-30E, the incision points were tracked and located only once during the start of the experiments. This is acceptable in case of robot-assisted MIS as shown in FIGS. 30A-30E as the remote center of motion is maintained at the incision point. The incision points marked at the beginning of the robotic surgery using the optical tracking system remain stationary. However, during manual surgery as shown in FIGS. 29A-29D, the incision points need to be tracked continuously by the optical tracking system. This limitation can be overcome by tracking frames that are attached to the trocars. The optical tracking system continuously tracks these frames and triangulates the positions of the incision points during the surgery as depicted in FIG. 7A and FIG. 10.

Second Testing of Tele-Mentoring Framework

To evaluate the performance of the tele-mentoring setups within and across geographical boundaries, the prototype was tested under two modes of operation. In Mode-I, the operating room workstation and remote location workstation were both located in the same city, Doha, Qatar. In Mode-II, the operating room workstation was situated in Doha, Qatar, while the remote location workstation was in Houston, Texas, USA.

An internet connection was used to connect both the workstations. The data sent and received by the networking threads on the workstations were logged and processed to evaluate the functioning of the tele-mentoring framework over the network. To avoid interferences caused by writing of the data onto a secondary storage, a queue was maintained in primary memory. The data to be logged was pushed into the queue, and removed to be written onto a secondary storage using an alternate thread.

The clocks on the remote and operating room workstations were synchronized from a common Network Time Protocol (NTP) server 216.239.35.4. The server synchronizes times among the connected workstation to within a few milliseconds. However, because of asymmetric routes and network congestion, the time difference between the workstation and its NTP server clock may be up to few milliseconds. This difference was incorporated in the calculations to measure the clock drift between the operating room workstation and remote location workstation. The clock drift was computed as:

$$\text{Clock Drift} = \Delta t_{NTP\text{-}Remote} - \Delta t_{NTP\text{-}OperatingRoom}$$

Where, $\Delta t_{NTP\text{-}Remote}$ denotes the time difference between the NTP server and the operating room workstation and $\Delta t_{NTP\text{-}OperatingRoom}$ denotes the time difference between the NTP server and the operating room workstation. The Clock Drift was added to the timestamps of the logged data to ensure synchronization between the clocks of the operating room and remote location workstations.

Results and Discussion of the Second Testing

The delay for sending the information from operating room to the remote location should be minimum. The major component of this information comprises of surgical scope camera poses $M_{ScopeCamera}(t)$ with the operating field video frame $F_{SurgicalView}(t)$.

Figure 35A:
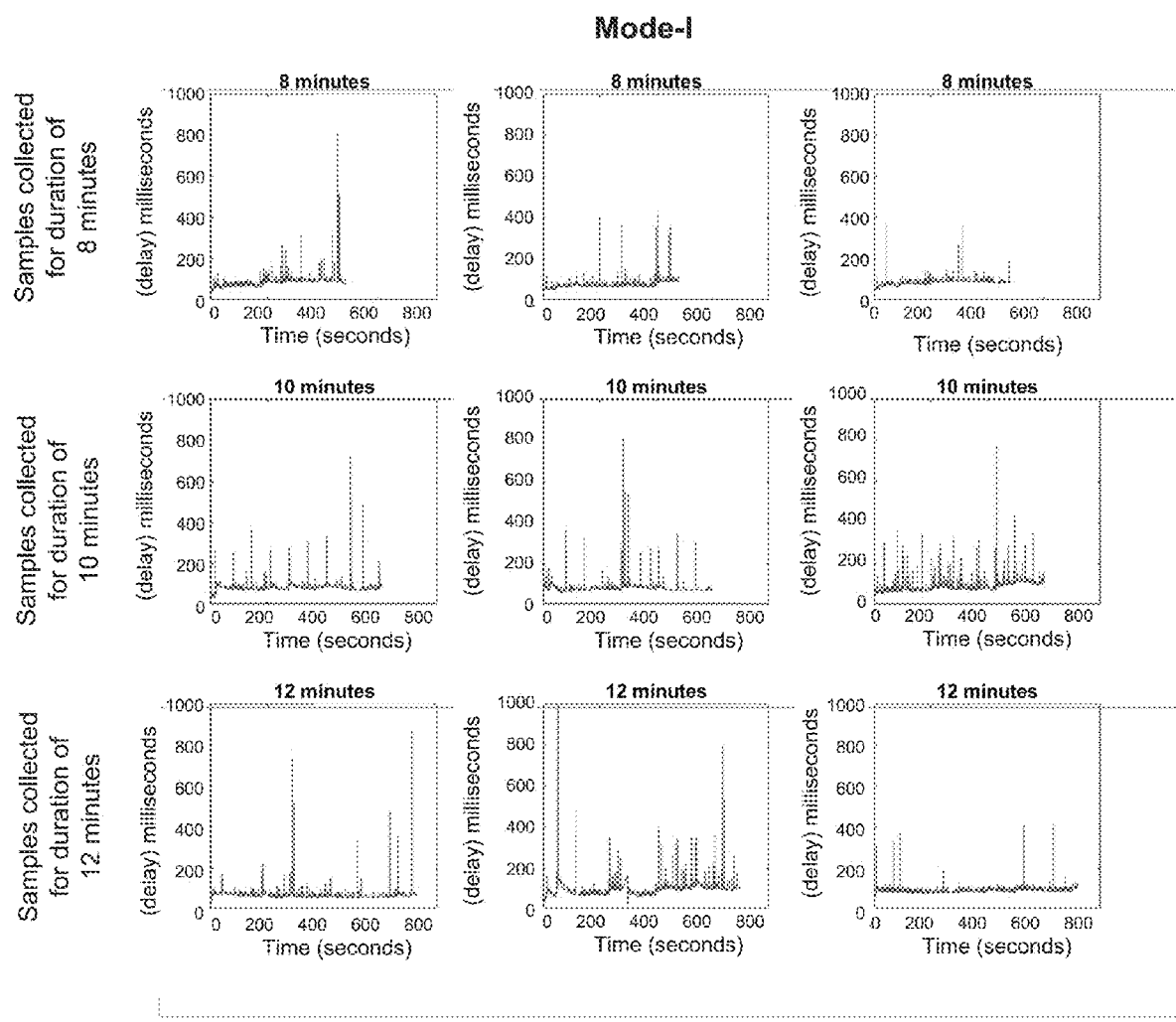
FIGS. 35A-43 illustrate data related to a second testing of tele-mentoring workstations as shown in FIGS. 29A-29E and FIGS. 30A-30E.
Figure 35B:
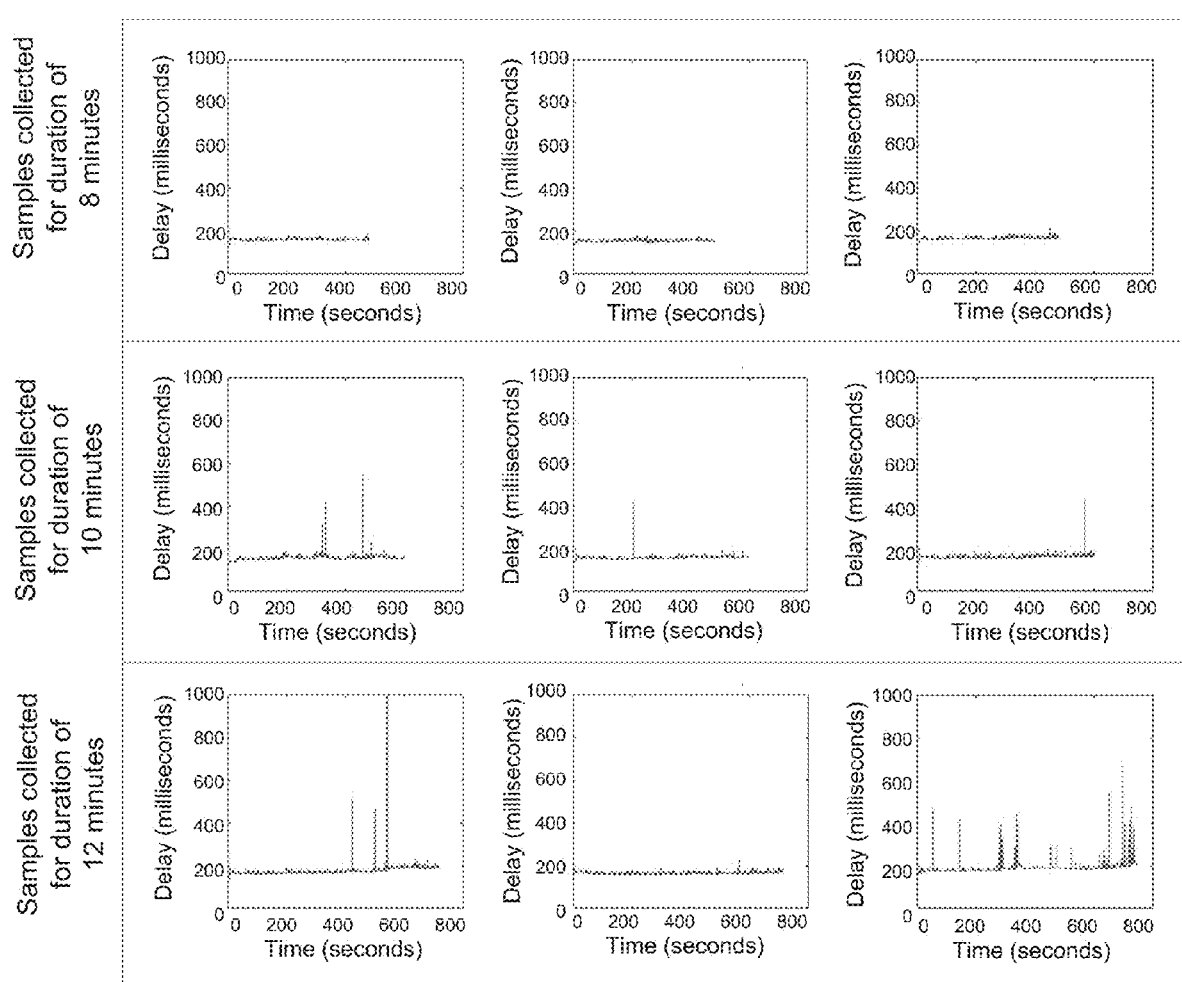

FIGS. 35A and 35B present the delay in transferring surgical scope camera poses $M_{ScopeCamera}(t)$ along with operating field video frame $F_{SurgicalView}(t)$ from operating room to the remote location workstation. Performance under each mode was evaluated for different time durations (varying from 8 to 12 minutes) with multiple trials (n=3). Mode-I and Mode-II average delays were 78.08±7.48 milliseconds and 163±12.42 milliseconds, respectively.

Figure 36A:
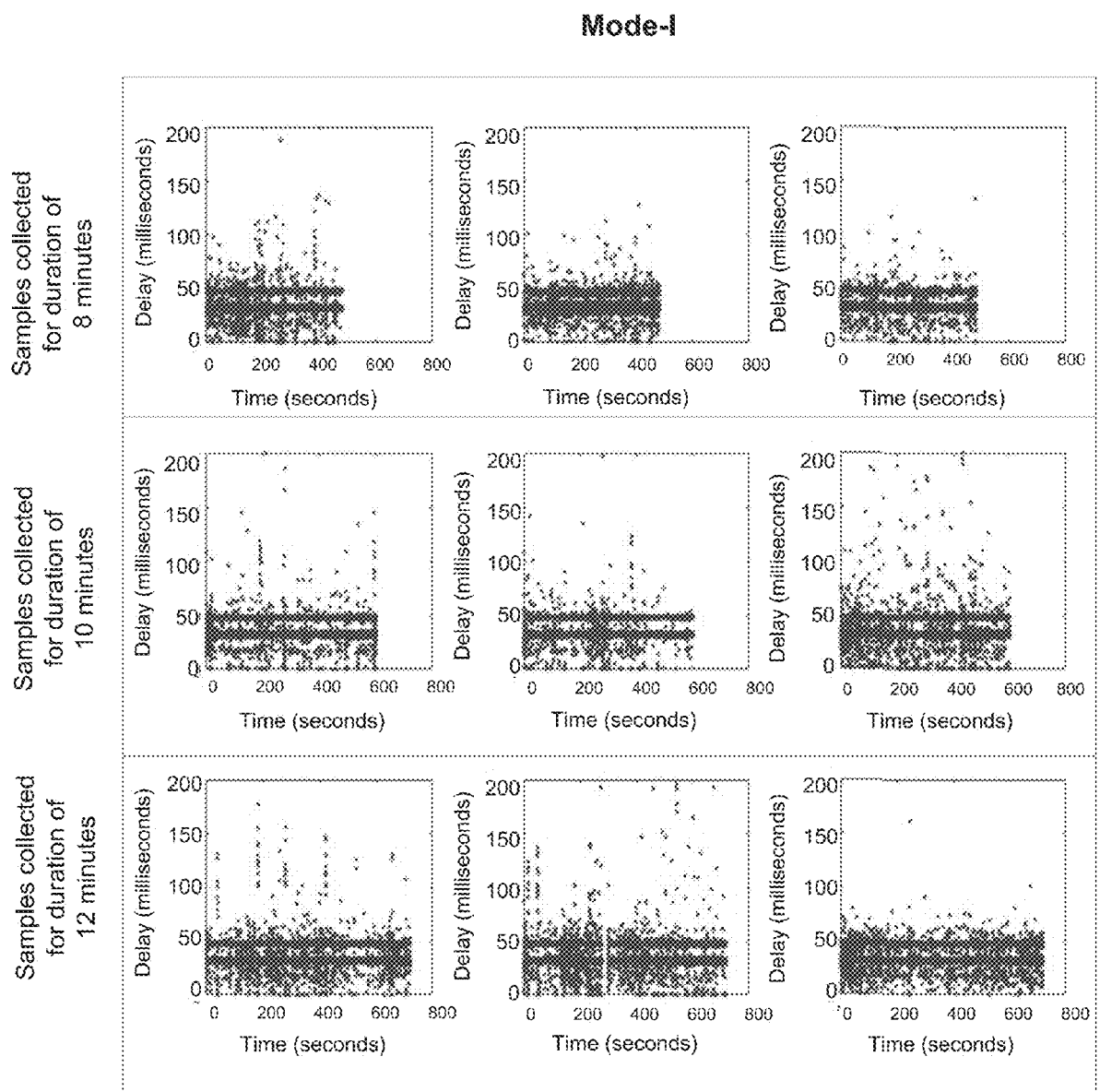
Figure 36B:
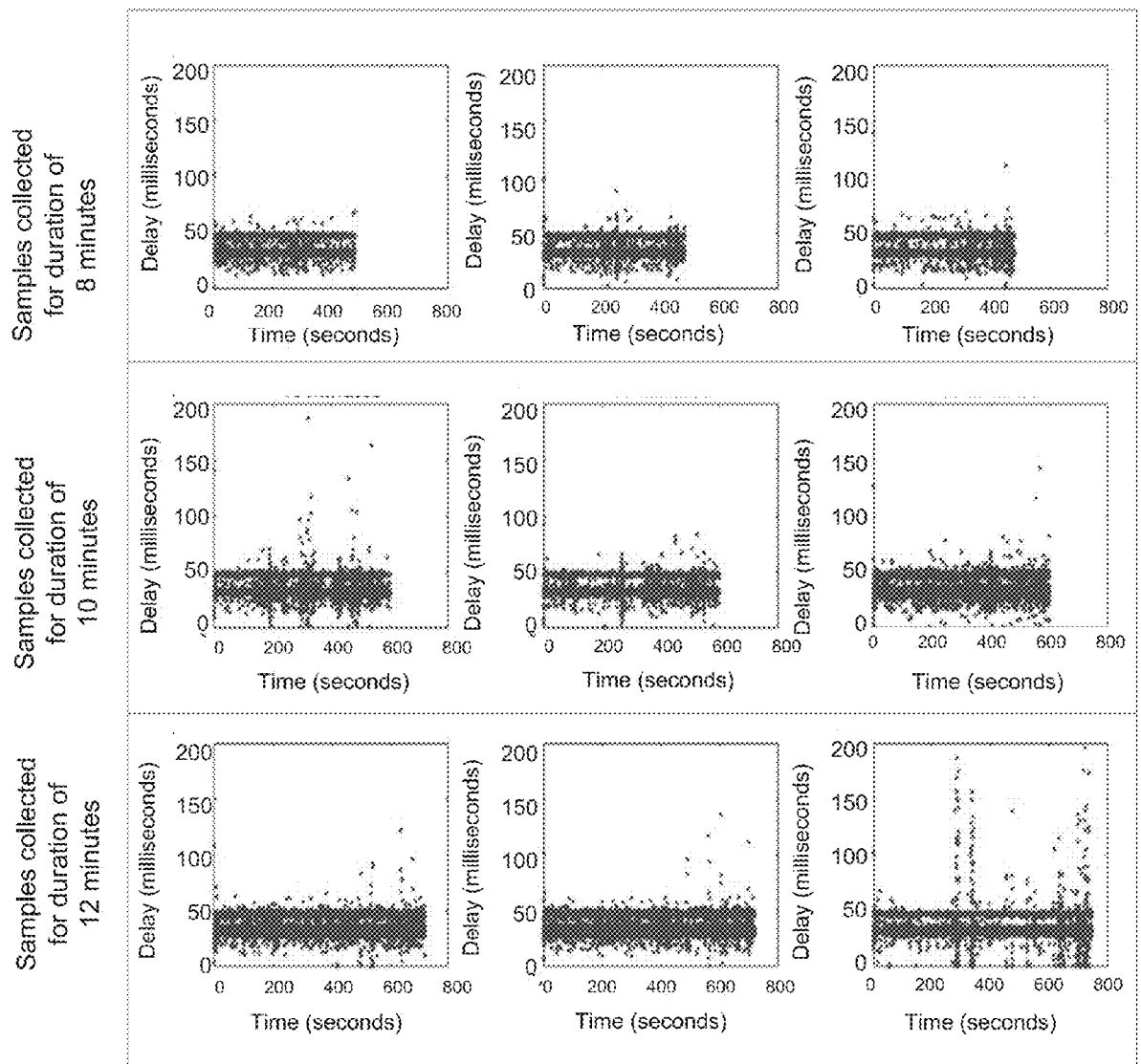

FIGS. 36A and 36B illustrate the frequency at which the scope camera poses $M_{ScopeCamera}(t)$ and operating field video frame $F_{SurgicalView}(t)$ are received at the operating room workstation. The average time duration in receiving two consecutive data packets one-after-another at the remote workstation was 33.47±27.21 milliseconds for Mode-I and 33.34±6.87 milliseconds for Mode-II.

Figure 37A:
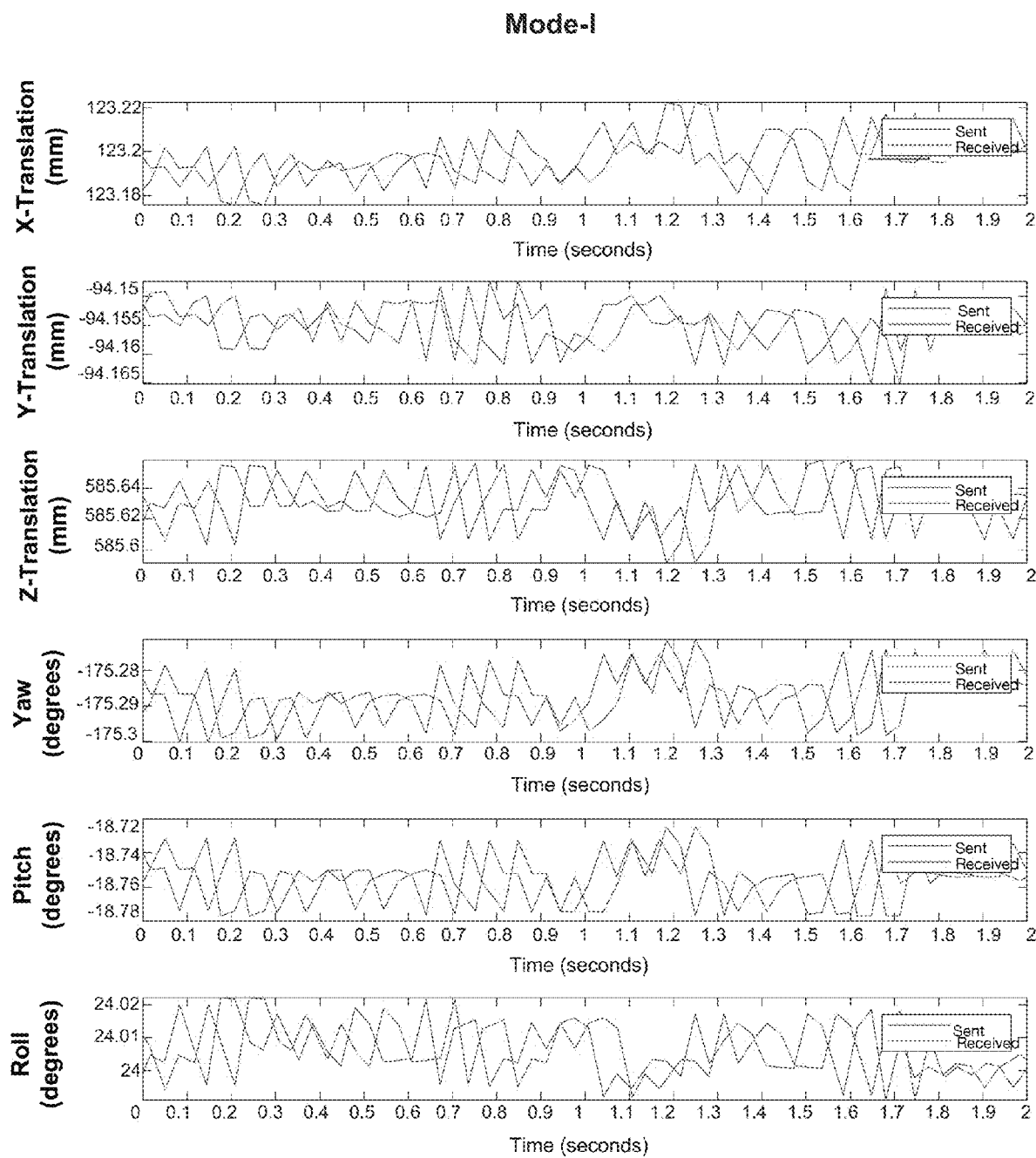
Figure 37B:
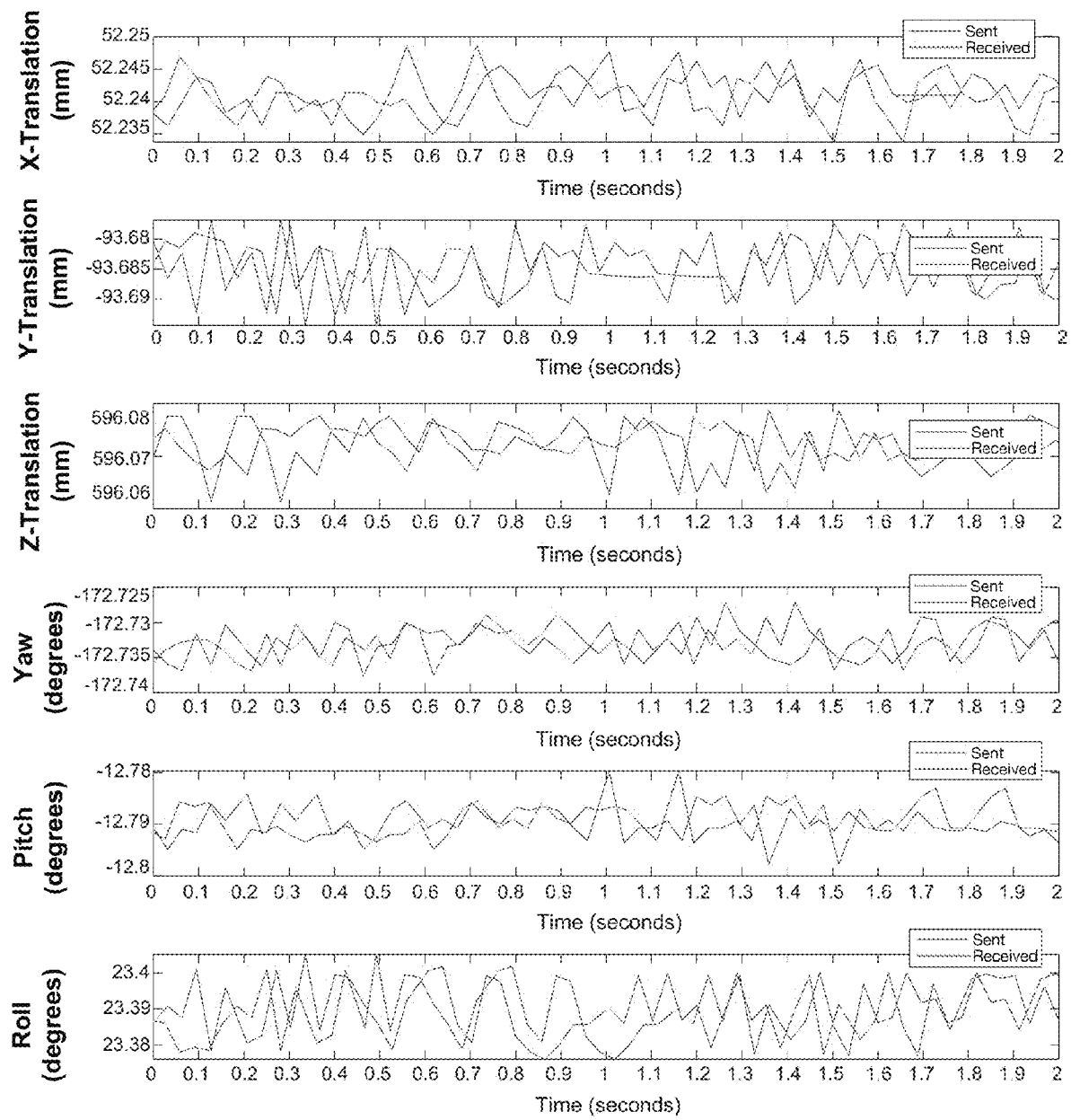

FIGS. 37A and 37B present the motion of the surgical scope in the operating room as replicated at the remote location for minor perturbations. The motion is represented in terms of signal generated for the surgical scope camera poses $M_{ScopeCamera}(t)$ over a duration of 5 seconds. The pose is composed of position (translations in X, Y, and Z direction) and orientation (rotations in form of roll, yaw, and pitch angles) of the scope camera. The networking video thread running on the operating room workstation sends the surgical scope camera pose, which is received by the networking video thread at the remote location workstation. The tele-mentoring prototype is able to detect these minor perturbations and sent the data over the network for both networking scenarios.

The latency in sending the video frame from operating room to remote location was analyzed along with the degradation in the quality of the frame causes by encoding-decoding. The frame of the operating field is encoded at the operating room workstation, send over the network, and then decoded at the remote location workstation.

Figure 38:
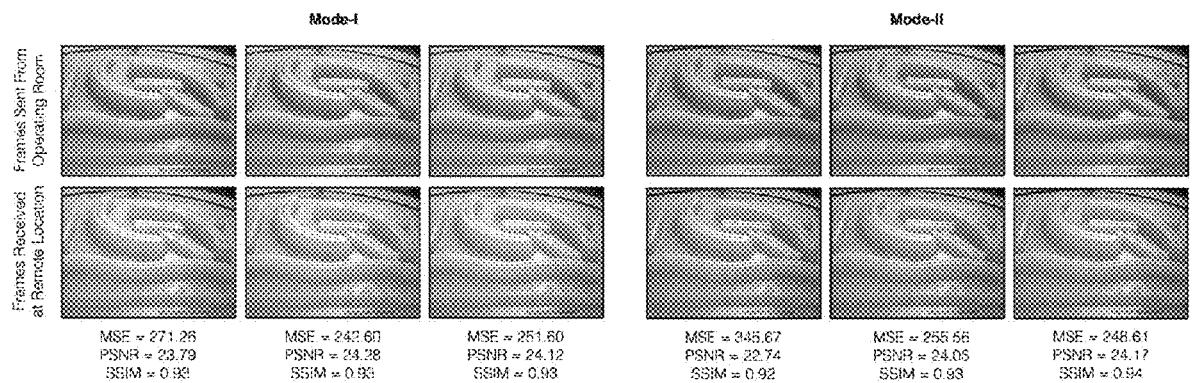
Figure 39:
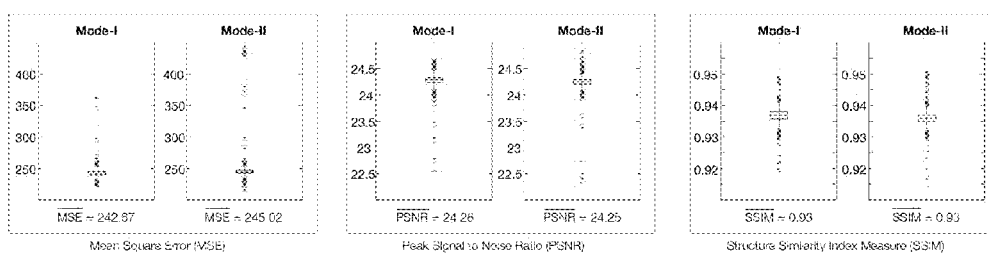

FIG. 38 shows a visual comparison of the operating field video frame sent by the operating room workstation before encoding and the corresponding frame received at the remote location workstation after decoding in Mode-1 and Mode-II of operation. Three frame pair samples for each mode were selected randomly from the video stream. The quality of sent frames (before encoding) and received frames (after decoding) were compared using the video image quality metrics as presented in FIG. 39.

The information to be sent from the remote location to the operating room primarily consist of motion of the augmented surgical instrument by the network data thread. The augmented surgical instrument motion is computed based on the poses of the surgical tooltips over time. The motion is intermittent as it is performed only when mentor needs to demonstrate the surgical tool motion to the mentee.

Figure 40:
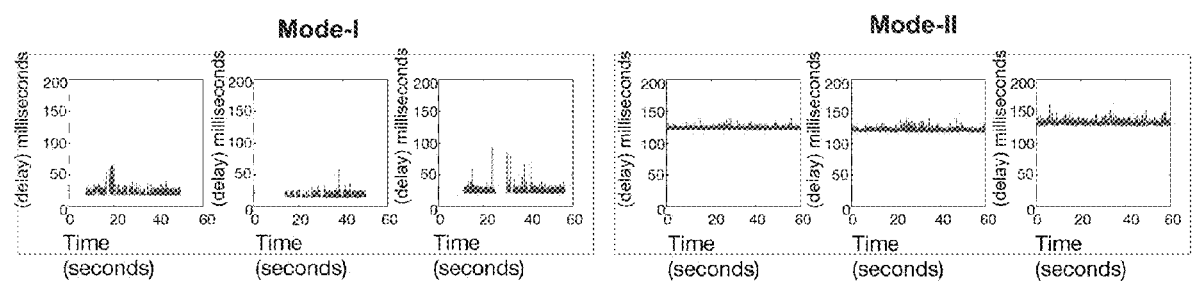

FIG. 40 presents the delay in transferring the surgical tooltips poses $M_{Tooltips}(t)$ from the remote location to the operating room under each mode. Each mode was evaluated for three trials. Mode-I and Mode-II average delays were 21.61±2.13 milliseconds and 132.87±23.15 milliseconds, respectively.

Figure 41:
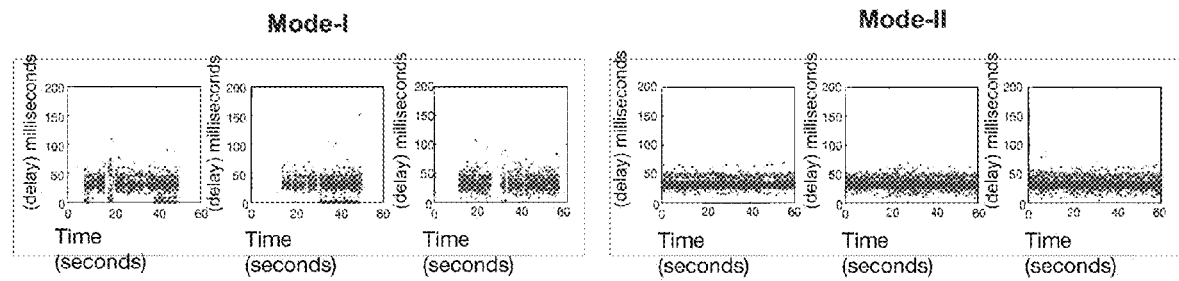

The frequency at which the surgical tooltips poses $M_{Tooltips}(t)$ are received at the remote location workstation was also measured, as shown is FIG. 41. Under each mode, three samples were collected for a duration of one minute. At the operating room workstation, the average time duration in receiving two consecutive data packets one-after-another was 26.59±15.26 milliseconds for Mode-I and 33.33±8.17 milliseconds for Mode-II.

Figure 42A:
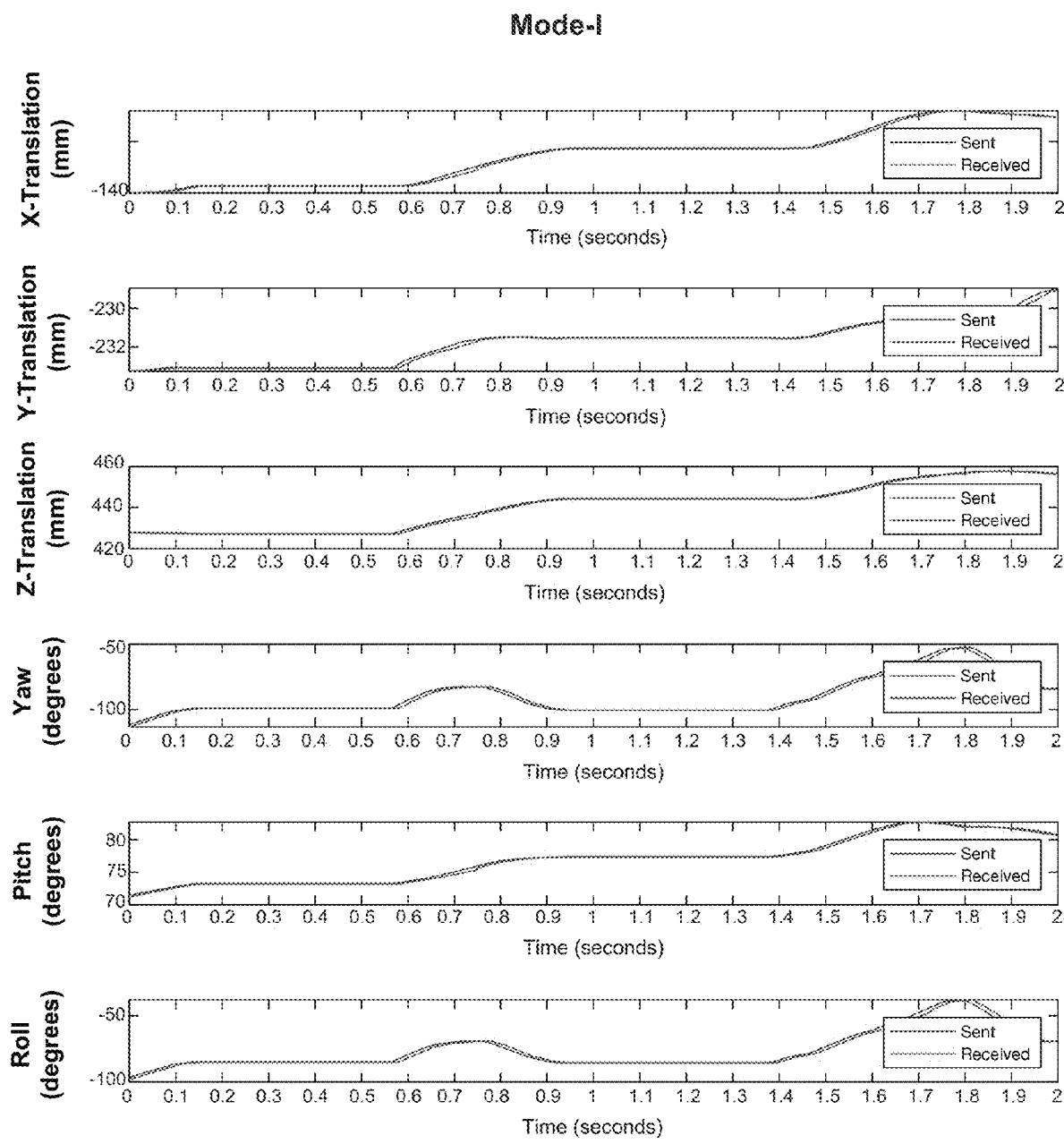
Figure 42B:
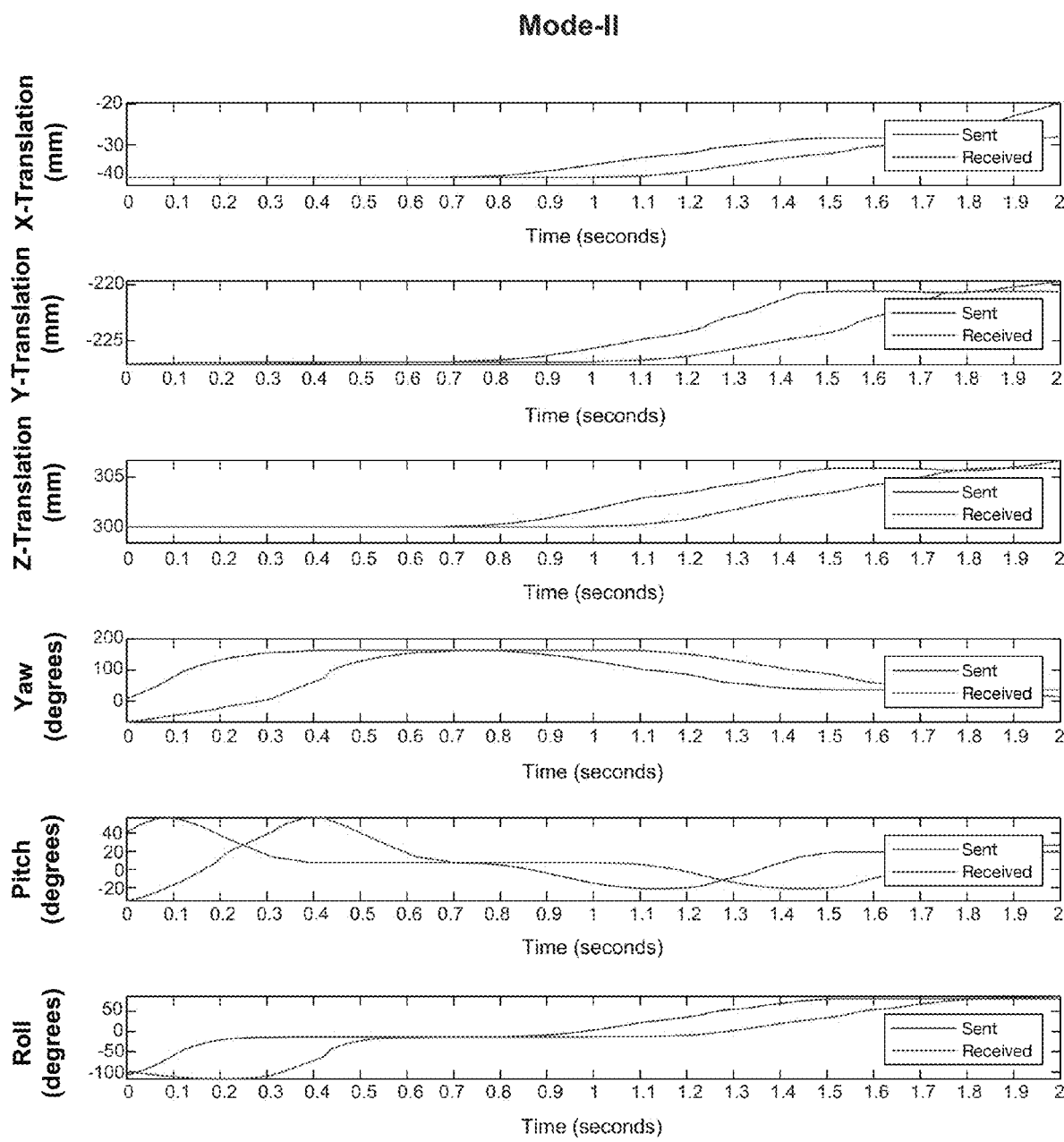
Figure 43:
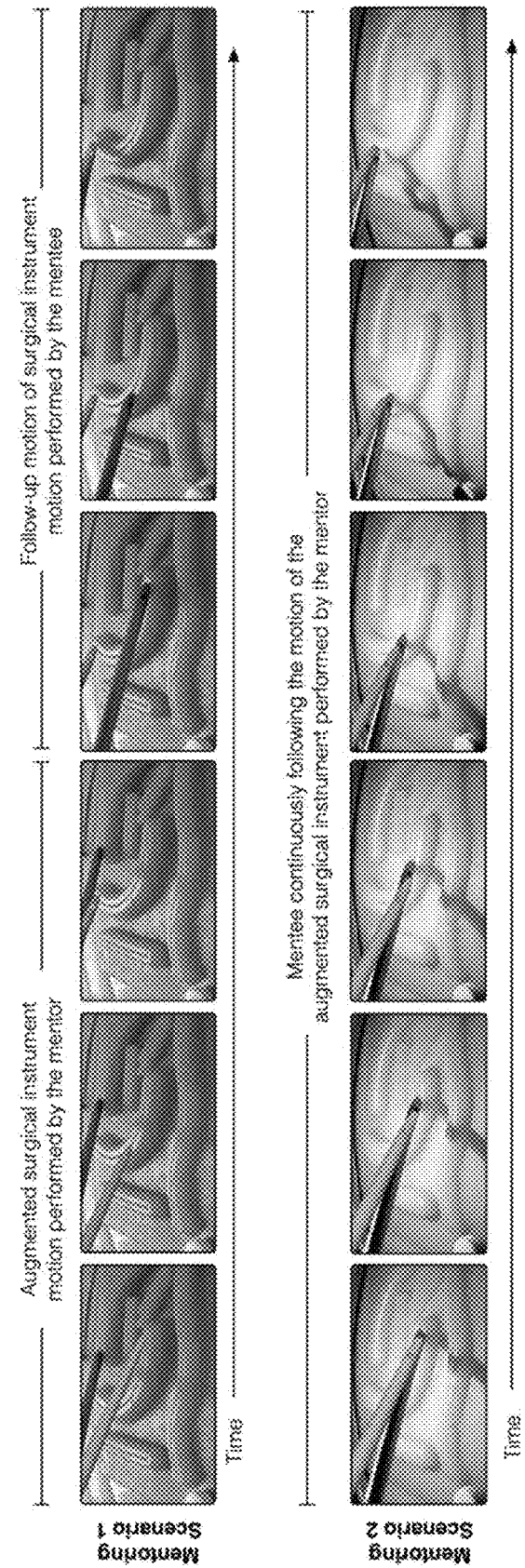

FIGS. 42A and 42B present the motion of the augmented surgical tool, expressed as position (translations in X, Y, and Z direction) and orientation (rotations in form of roll, yaw, and pitch angles) of the surgical tooltips poses $M_{Tooltips}(t)$ for a duration of two seconds. The communication between the mentor and mentee can occur in two possible ways as illustrated in FIG. 43. In Mentoring Scenario 1, the mentor simply demonstrates the complete surgical tooltip motion and then the mentee follows it. In Mentoring Scenario 2, the mentee continuously follows the motion performed by the mentor.

Further Considerations

For surgical tele-mentoring, there are several conceptual frameworks and learning theories. Integration of the proposed technology in a structured surgical tele-mentoring curriculum would require engagements on four fronts. First, as a prerequisite, the mentor apart from having surgical and educational expertise, needs to be trained on using the interfaces of the proposed tele-mentoring framework provided at the remote location. On other hand, the mentee should be able to understand the augmented surgical tool motions visualized on the operating field and replicate it. Second, as the proposed tele-mentoring framework is introduced as a new teaching modality, it should be tailored to suit the surgical setting. It would also require simulation based training and orientation of the proposed tele-mentoring framework. Third as part of a curriculum, the curriculum components should focus on the technology including communication and troubleshooting. The mentor-mentee need to have a structured method of communication. For example, if a tool motion is demonstrated by the mentor along with audio cues, as reciprocal the mentee should move the tools and stop when needed. In addition to a standardized lexicon, protocols would be required to troubleshoot in case of obstacles to ensure smooth communication. Finally, on assessment methods fronts, apart from traditional methods (360-degree feedback and video based review), the proposed telemedicine technology can log and assess the way mentor wanted to move the tool and the way mentee moved it.

The future work for further improving the tele-mentoring framework will be geared towards three main aspects. First, the tele-mentoring framework tracks the scope poses and incision points and uses the information to generate a virtual 3D environment of the surgical field. However, in certain minimally invasive surgeries, such as or single incision surgery with actuated scopes and instruments, the current tracking setup is not sufficient due to occlusion causes in the line of sight of the optical tracking system. Additional tracking mechanisms 61, such as electromagnetic tracking systems (e.g. Patriot™ by Polhemus, USA), ultrasonic sensors, or mechanical arms with inbuilt gimbal mechanism need to be integrated with the tele-mentoring framework. This will assist to track (a) poses of the camera and (b) positions of the incision points or even the poses from where instruments exist flexible endo-luminal cannulas inside the patient's body. Secondly, the current implementation facilitates transfer of surgical field and augmented data in the form of visual cues. Another aspect, which is as crucial as visual cues, is the exchange of audio between the operating and mentoring surgeon. The future iteration of the tele-mentoring framework will need to have audio and visual cues transferred over the network in synchronization. This could be achieved by using audio codecs such as advanced audio coding (AAC) with RTMP server. Another option is to replace RTMP with webRTC, which internally uses SRTP. The protocol adds sequence numbers/time stamps/unique stream IDs, which is used to ensure synchronization between audio and video streams. We also plan to optimize the network components and test it across multiple networks. Lastly, clinical studies will be required to assess the knowledge transferred using the tele-mentoring framework, especially with respect to the motion of augmented surgical tools, and its applicability in different surgical sub-specialties.

The present technology, in an embodiment, would overcome the limitation of existing solutions by transforming hand gestures or hand motion of the remote surgeon into virtual surgical tooltip movements using low-cost interface and superimposing it on the local surgeon's view of the surgical field. These dynamic virtual tools would be highly-articulated in nature and would exhibit all possible movement in the three-dimensional space. The present technology, in an embodiment, would ease the understanding and facilitate knowledge transfer by directly displaying the exact interaction required. Thus, the present technology, in an embodiment, would fundamentally change the current augmented-reality based tele-collaboration or tele-mentoring methodologies and would expand its scope to MIS by providing better realistic visual cues.

Further, the present technology, in an embodiment, would enable remote collaboration between surgeons for minimally invasive surgical procedures using augmented reality. The technology becomes crucial especially in those scenarios where the patient needs to undergo a surgical procedure and the specialist surgeon is not present on-site. Using the present technology, real-time, interactive, intraoperative guidance from a remotely located expert surgeon will be available during the minimally invasive surgical procedure according to an embodiment. As an expert surgeon is guiding the procedure and providing assistance/input step-by-step, the surgical outcome would be improved for the patient. Moreover, as the technology is not restricted to a particular surgery type, it can be adapted and used across different surgical departments in the hospital. As more and more departments use the technology, the number of patients benefited from the technology would also increase.

Furthermore, the present technology would serve as training tool for a local surgeon to get trained on new minimally invasive surgical techniques/surgical workflows by a remote specialized surgeon according to an embodiment. This would in turn expand the range of surgical services offered by the hospital and improve the capacity building of the health care system. It would also save the time and cost on logistics (such as travel, stay, and cost per day) for inviting an expert surgeon. Additionally, as the local surgeons become specialized and experienced, they can impart the learned skills as remote services using the same technology. This would expand the reach of the hospital across geographical boundaries, generate new income streams, and eventually transform it into a global hub.

It should be noted that as the systems used in MIS continue to evolve, the basic mechanism for patient-surgeon interaction remains the same (i.e. in a typical setup, the surgeon operates on the patient using manual-operated or robotically-actuated tooltips inserted through small incision and visualizes the tool-tissue interaction on a screen using a miniature camera). Therefore, as new instruments or robotic systems for minimally invasive surgery are introduced to the healthcare market, the present technology can still be applied by simply loading the design and kinematics of these tools in the software according to an embodiment. The adaptability to the evolving healthcare market place will support the widest possible range of manual or robot-assisted MIS and offer a modular/expandable platform to support future needs according to an embodiment.

As used herein and in the appended claims, the singular form of a word includes the plural, unless the context clearly dictates otherwise. Thus, the references "a," "an" and "the" are generally inclusive of the plurals of the respective terms. For example, reference to "an ingredient" or "a method" includes a plurality of such "ingredients" or "methods." The term "and/or" used in the context of "X and/or Y" should be interpreted as "X," or "Y," or "X and Y."

Similarly, the words "comprise," "comprises," and "comprising" are to be interpreted inclusively rather than exclusively. Likewise, the terms "include," "including" and "or" should all be construed to be inclusive, unless such a construction is clearly prohibited from the context. However, the embodiments provided by the present disclosure may lack any element that is not specifically disclosed herein. Thus, a disclosure of an embodiment defined using the term "comprising" is also a disclosure of embodiments "consisting essentially of" and "consisting of" the disclosed components. Where used herein, the term "example," particularly when followed by a listing of terms, is merely exemplary and illustrative, and should not be deemed to be exclusive or comprehensive. Any embodiment disclosed herein can be combined with any other embodiment disclosed herein unless explicitly indicated otherwise.

The term "patient" is understood to include an animal, especially a mammal, and more especially a human that is receiving or intended to receive treatment, as treatment is herein defined. While the terms "individual" and "patient" are often used herein to refer to a human, the present disclosure is not so limited. Accordingly, the terms "individual" and "patient" refer to any animal, mammal or human that can benefit from the treatment.

The relative terms "improved," "increased," "enhanced" and the like refer to the effects of the methods and compositions disclosed herein.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention claimed is:

1. A method comprising:
   connecting a local workstation and a remote workstation;
   providing to at least one of the local workstation or the remote workstation at least one of an instrument state or a scope state
   and at least one of a trocar, a trocar tracking frame attached to the trocar, a scope, or a scope tracking frame attached to the scope; and
   continuously updating at least one of a surgical state, a tooltip pose, data to be communicated over network, or a rendered object on a visualization screen in each of the local and remote workstations;
   wherein the scope state comprises at least one of the scope's field of view (FOV), the scope's angulation, and transformation between MScope(t) and MScopeCamera(t),
   wherein MScope(t) represents a pose of the scope tracking frame attached to the scope in form of 4×4 homogenous transformation matrix for time instant "t," and
   MScopeCamera(t) represents a pose of scope camera is represented by 4×4 homogenous transformation matrix at time instant "t".

2. The method of claim 1 comprising providing the trocar and further comprising providing a label indicating a position of the trocar.

3. The method of claim 2 further comprising mapping at least one of a instrument type or a human computer interface to the label.

4. The method of claim 3 comprising mapping the human computer interface to the label.

5. The method of claim 4 further comprising interacting with the human computer interface and updating the tooltip pose of a rendered augmented tool on both the local and remote workstations.

6. The method of claim 1, wherein the instrument state comprises a list of instruments to be used.

7. The method of claim 1, wherein the at least one of the instrument state and the scope state is shared by both the local workstation and the remote workstation.

8. The method of claim 1 comprising rendering an augmented-reality scene on a visualization screen.

9. A system comprising:
   a local system comprising
      an input/output device selected from the group consisting of a microphone, a speaker, a first visualization screen, and combinations thereof,
      a scope system comprising at least one of a scope, a camera, a camera system, a scope's tracking frame, and combinations thereof,
      an optical tracking system,
      a trocar system comprising at least one of a trocar, a trocar's tracking frame, and combinations thereof; and
   a remote system connected to the operating room system via a network, the remote system comprising a human computer interface system comprising at least one of a camera, a sensor, a user interface, and combinations thereof, a second visualization screen.

10. The system of claim 9, wherein the local system further comprises an operating instrument.

11. A method for remote collaboration and training, the method comprising:

transforming a hand gesture of a first user into a virtual tooltip movement;

superimposing the virtual tooltip movement on a second user's view of a visual field;

receiving a video frame;

extracting an actual tooltip from the video frame to form the virtual tooltip;

computing a position of the actual tooltip;

calibrating the position of the virtual tooltip from the hand gesture with the actual tooltip from the video stream; and rendering a complete virtual tool if the actual tooltip and the virtual tooltip are aligned, or rendering only the virtual tooltip if the actual tooltip and the virtual tooltip are not aligned.

12. The method of claim 11, wherein transforming the hand gesture of the first user into the virtual tooltip movement comprises extracting a position of at least one optical marker attached to a grasper in the first user's hand and triangulating the position into a position of the virtual tooltip.

13. The method of claim 11 comprising rendering the virtual tooltip movement generated by the first user along with a video stream from a scope's camera on a visualization screen.

14. The method of claim 11 comprising transmitting a live video stream from the first user's workstation to the second user's workstation over a network.

15. A system for remote collaboration and training, the system comprising:

a first computing system comprising first I/O devices configured for a first user to receive and send information;

a second computing system comprising second I/O devices for a second user to receive and send information, wherein the first and second I/O devices are each selected from the group consisting of an infrared camera configured to capture the second user's hand gestures holding an instrument, the instrument, a scope configured to capture a video of a visual field of the first user, a first visualization screen configured to display the video of the visual field, a second visualization screen configured to display an augmented visual field, and combinations thereof;

a module configured to operate on at last one of the first or second computing systems, wherein the module is selected from the group consisting of a video processing module configured to receive a video frame from a network module, extract an actual tooltip from the video frame, and compute a position of the tooltip, a control logic module configured to take a first input from the video processing module and a reconstruction module and provide a second input to an augmentation module on graphical rendering;

an augmentation module configured to render an augmented-reality scene on the second visualization screen, the reconstruction module configured to transform the second user's hand gestures into movements of a virtual tooltip, the network module configured to exchange data over a network connecting the first and second computing system, and combinations thereof.

16. The system of claim 15, wherein the second I/O devices comprise the infrared camera, and the instrument comprises a grasper.

17. The system of claim 16, wherein the grasper comprises a pinching member configured to constrain a motion of the second user's hand holding the grasper and at least one optical marker configured to trace the motion of the second user's hand and at least one of opening or closing of the grasper in the infrared camera.

18. The system of claim 17, wherein the pinching member is configured to constrain a motion of the second user's index finger and thumb with respect to each other.

19. The system of claim 15, wherein the reconstruction module is configured to transform the second user's hand gestures into movements of the virtual tooltip by extracting a position of the at least one optical marker attached to the grasper and triangulating the positions into a position of the virtual tooltip.

20. The system of claim 15, wherein the control logic module is configured to calibrate the position of the virtual tooltip from the second user's hand gestures with an actual tooltip from the video stream.

21. The system of claim 15, wherein the augmentation module is configured to receive an input in a form of video frame from the network module and decision to render a tooltip or complete tool from the control logic module.

22. The system of claim 15, wherein the augmentation module is configured to, based on the input, render the augmented reality scene consisting of three-dimensional computer graphics rendered on the video stream.

23. The system of claim 15, wherein the augmentation module comprises an inverse kinematics sub-module configured to compute the position of the virtual tooltip.

24. The system of claim 23, wherein the position of the virtual tooltip comprises at least one of a degree-of-freedoms or a base frame.

25. A method comprising:

receiving a video frame including an actual tooltip, extracting the actual tooltip from the video frame, and computing a position of the actual tooltip, by a video processing module of a computing system comprising at least one processor and a data storage device in communication with the at least one processor;

receiving an input from the video processing module and a reconstruction module and providing the input to an augmentation module on graphical rendering, by a control logic module of the computing system;

rendering, by the augmentation module of the computing system, an augmented-reality scene on a first visualization screen;

transforming a user's hand gestures into movements of a virtual tooltip, by the reconstruction module of a computing system;

exchanging data, by a network module of the computing system, over a network.

26. The method of claim 25 further comprising:
capturing, by an infrared camera, the user's hand gestures simulating the holding of the actual tooltip;
capturing, by a scope, a video of a visual field; and
displaying the video of the visual field on the first visualization screen.

27. The method of claim 25 further comprising:
calibrating the position of the virtual tooltip from the user's hand gestures with the actual tooltip from the video frame; and
rendering a complete virtual tool if the actual tooltip and the virtual tooltip are aligned, or rendering only the virtual tooltip if the actual tooltip and the virtual tooltip are not aligned.

* * * * *